(12) United States Patent
Racenet et al.

(10) Patent No.: US 8,033,439 B2
(45) Date of Patent: *Oct. 11, 2011

(54) SURGICAL STAPLING DEVICE

(75) Inventors: David C. Racenet, Litchfield, CT (US); Timothy N. Wells, Manchester, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/904,566

(22) Filed: Sep. 27, 2007

(65) Prior Publication Data

US 2008/0023523 A1    Jan. 31, 2008

Related U.S. Application Data

(63) Continuation of application No. 11/436,282, filed on May 18, 2006, now Pat. No. 7,275,674, which is a continuation of application No. 11/125,790, filed on May 10, 2005, now abandoned, which is a continuation of application No. 10/783,126, filed on Feb. 20, 2004, now abandoned, which is a continuation of application No. 09/687,815, filed on Oct. 13, 2000, now Pat. No. 6,817,508.

(51) Int. Cl.
*A61B 17/072* (2006.01)
(52) U.S. Cl. ............... 227/176.1; 227/19; 227/175.1
(58) Field of Classification Search .......... 227/19, 227/175.1, 176.1, 178.1
See application file for complete search history.

(56) References Cited

U.S. PATENT DOCUMENTS

| | | | |
|---|---|---|---|
| 2,174,219 | A | 3/1939 | Balma |
| 3,079,606 | A | 3/1963 | Bobrov et al. |
| 3,080,564 | A | 3/1963 | Strekopytov et al. |
| 3,252,643 | A | 5/1966 | Strekopytov et al. |
| 3,269,630 | A | 8/1966 | Fleischer |
| 3,317,105 | A | 5/1967 | Astafjev et al. |
| 3,494,533 | A | 2/1970 | Green et al. |
| 3,692,224 | A | 9/1972 | Astafiev et al. |
| 3,795,034 | A | 3/1974 | Strekopytov et al. |
| 3,822,818 | A | 7/1974 | Strekopytov et al. |
| 4,047,654 | A | 9/1977 | Alvarado |
| 4,216,891 | A | 8/1980 | Behlke |
| 4,244,372 | A | 1/1981 | Kapitanov et al. |

(Continued)

FOREIGN PATENT DOCUMENTS

EP    0136950    4/1985

(Continued)

OTHER PUBLICATIONS

Information Booklet for Auto Suture, Poly CS-57, Disposable Surgical Stapler, 1988, USSC.

(Continued)

*Primary Examiner* — Paul Durand
*Assistant Examiner* — Nathaniel Chukwurah

(57) ABSTRACT

A surgical stapling device for applying an array of surgical staples to tissue is provided. The stapling device includes an approximation mechanism for moving a cartridge assembly and an anvil assembly between spaced and approximated positions and a firing mechanism for ejecting the array of staples from the cartridge assembly. A single trigger is operable to effect approximation and firing of the device. The device also includes an alignment pin assembly which can be selectively manually or automatically advanced. The anvil assembly includes a stiffener plate which allows the device to have a reduced head portion profile.

42 Claims, 23 Drawing Sheets

U.S. PATENT DOCUMENTS

| | | |
|---|---|---|
| 4,296,881 A | 10/1981 | Lee |
| 4,305,539 A | 12/1981 | Korolkov et al. |
| 4,354,628 A | 10/1982 | Green |
| 4,378,901 A | 4/1983 | Akopov et al. |
| 4,383,634 A | 5/1983 | Green |
| 4,402,445 A | 9/1983 | Green |
| D273,513 S | 4/1984 | Spreckelmeier |
| 4,442,964 A | 4/1984 | Becht |
| 4,470,533 A | 9/1984 | Schuler |
| 4,475,679 A | 10/1984 | Fleury, Jr. |
| 4,506,670 A | 3/1985 | Crossley |
| 4,506,671 A | 3/1985 | Green |
| 4,508,253 A | 4/1985 | Green |
| 4,513,746 A | 4/1985 | Aranyi et al. |
| 4,520,817 A | 6/1985 | Green |
| 4,522,327 A | 6/1985 | Korthoff et al. |
| 4,527,724 A | 7/1985 | Chow et al. |
| 4,530,453 A | 7/1985 | Green |
| 4,566,620 A | 1/1986 | Green et al. |
| 4,568,009 A | 2/1986 | Green |
| 4,573,622 A | 3/1986 | Green et al. |
| 4,580,712 A | 4/1986 | Green |
| 4,585,153 A | 4/1986 | Failla et al. |
| D283,733 S | 5/1986 | Rawson et al. |
| 4,589,582 A | 5/1986 | Bilotti |
| 4,591,085 A | 5/1986 | DiGiovanni |
| 4,605,004 A | 8/1986 | DiGiovanni et al. |
| 4,606,344 A | 8/1986 | DiGiovanni |
| 4,606,345 A | 8/1986 | Dorband et al. |
| 4,607,636 A | 8/1986 | Kula et al. |
| 4,612,933 A | 9/1986 | Brinkerhoff et al. |
| 4,617,928 A | 10/1986 | Alfrance |
| 4,632,290 A | 12/1986 | Green et al. |
| 4,635,634 A | 1/1987 | Santos |
| 4,665,916 A | 5/1987 | Green |
| 4,684,051 A | 8/1987 | Akopov et al. |
| 4,714,187 A | 12/1987 | Green |
| 4,715,520 A | 12/1987 | Roehr, Jr. et al. |
| 4,728,020 A | 3/1988 | Green et al. |
| 4,741,336 A | 5/1988 | Failla et al. |
| 4,767,044 A | 8/1988 | Green |
| 4,788,978 A | 12/1988 | Strekopytov et al. |
| 4,802,614 A | 2/1989 | Green et al. |
| 4,805,823 A | 2/1989 | Rothfuss |
| 4,809,898 A | 3/1989 | Gassner et al. |
| 4,819,853 A | 4/1989 | Green |
| 4,848,637 A | 7/1989 | Pruitt |
| 4,869,414 A | 9/1989 | Green et al. |
| 4,881,544 A | 11/1989 | Green et al. |
| 4,881,545 A | 11/1989 | Isaacs et al. |
| 4,915,100 A | 4/1990 | Green |
| 4,930,503 A * | 6/1990 | Pruitt .................. 227/178.1 |
| 4,938,408 A | 7/1990 | Bedi et al. |
| 4,941,623 A | 7/1990 | Pruitt |
| 4,951,861 A | 8/1990 | Schulze et al. |
| 4,964,559 A | 10/1990 | Deniega et al. |
| 5,005,754 A | 4/1991 | Van |
| 5,018,657 A | 5/1991 | Pedlick et al. |
| 5,027,834 A | 7/1991 | Pruitt |
| 5,071,052 A | 12/1991 | Rodak et al. |
| 5,100,042 A | 3/1992 | Gravener et al. |
| 5,116,349 A | 5/1992 | Aranyi |
| 5,137,198 A | 8/1992 | Nobis et al. |
| 5,172,845 A | 12/1992 | Tejeiro |
| 5,190,203 A | 3/1993 | Rodak |
| 5,219,111 A | 6/1993 | Bilotti et al. |
| 5,222,963 A | 6/1993 | Brinkerhoff et al. |
| 5,240,163 A | 8/1993 | Stein et al. |
| 5,344,060 A | 9/1994 | Gravener et al. |
| 5,368,599 A | 11/1994 | Hirsch et al. |
| 5,395,034 A | 3/1995 | Allen et al. |
| 5,405,073 A | 4/1995 | Porter |
| 5,413,267 A | 5/1995 | Solnytjes et al. |
| 5,439,155 A | 8/1995 | Viola |
| 5,445,304 A | 8/1995 | Plyley et al. |
| 5,452,836 A | 9/1995 | Huitema et al. |
| 5,458,279 A | 10/1995 | Plyley |
| 5,462,215 A | 10/1995 | Viola et al. |
| 5,464,144 A | 11/1995 | Guy et al. |
| 5,465,895 A | 11/1995 | Clark et al. |
| 5,470,006 A | 11/1995 | Rodak |
| 5,470,008 A * | 11/1995 | Rodak .................. 227/176.1 |
| 5,470,009 A | 11/1995 | Rodak |
| 5,480,089 A | 1/1996 | Blewett |
| 5,503,320 A | 4/1996 | Webster et al. |
| 5,509,596 A | 4/1996 | Green et al. |
| 5,542,594 A | 8/1996 | McKean et al. |
| 5,547,117 A | 8/1996 | Hamblin et al. |
| 5,558,266 A | 9/1996 | Green et al. |
| 5,579,978 A | 12/1996 | Green et al. |
| 5,580,067 A | 12/1996 | Hamblin et al. |
| 5,603,443 A | 2/1997 | Clark et al. |
| 5,605,272 A * | 2/1997 | Witt et al. .................. 227/175.2 |
| 5,605,273 A | 2/1997 | Hamblin et al. |
| 5,607,094 A | 3/1997 | Clark et al. |
| 5,615,820 A * | 4/1997 | Viola .................. 227/176.1 |
| 5,641,111 A | 6/1997 | Ahrens et al. |
| 5,673,842 A | 10/1997 | Bittner et al. |
| 5,678,748 A | 10/1997 | Plyley et al. |
| 5,697,543 A * | 12/1997 | Burdorff .................. 227/176.1 |
| 5,706,997 A | 1/1998 | Green et al. |
| 5,706,998 A | 1/1998 | Plyley et al. |
| 5,732,871 A | 3/1998 | Clark et al. |
| 5,735,445 A * | 4/1998 | Vidal et al. .................. 227/175.4 |
| 5,785,232 A | 7/1998 | Vidal et al. |
| 5,794,834 A | 8/1998 | Hamblin et al. |
| 5,810,240 A | 9/1998 | Robertson |
| 5,855,311 A | 1/1999 | Hamblin et al. |
| 5,878,937 A | 3/1999 | Green et al. |
| 5,893,506 A | 4/1999 | Powell |
| 5,894,979 A | 4/1999 | Powell |
| 5,964,394 A | 10/1999 | Robertson |
| 6,045,560 A | 4/2000 | McKean et al. |
| 6,817,508 B1 * | 11/2004 | Racenet et al. ............. 227/176.1 |
| 7,275,674 B2 * | 10/2007 | Racenet et al. ............. 227/175.1 |

FOREIGN PATENT DOCUMENTS

| | | |
|---|---|---|
| EP | 0220029 | 4/1987 |
| EP | 0273468 | 7/1988 |
| EP | 0537571 | 4/1993 |
| FR | 2542188 | 9/1984 |
| GB | 2141066 | 12/1984 |
| WO | WO 83/02247 | 7/1983 |

OTHER PUBLICATIONS

Proximate, RL Plus Reloadable Linear Stapler, instructions.

* cited by examiner

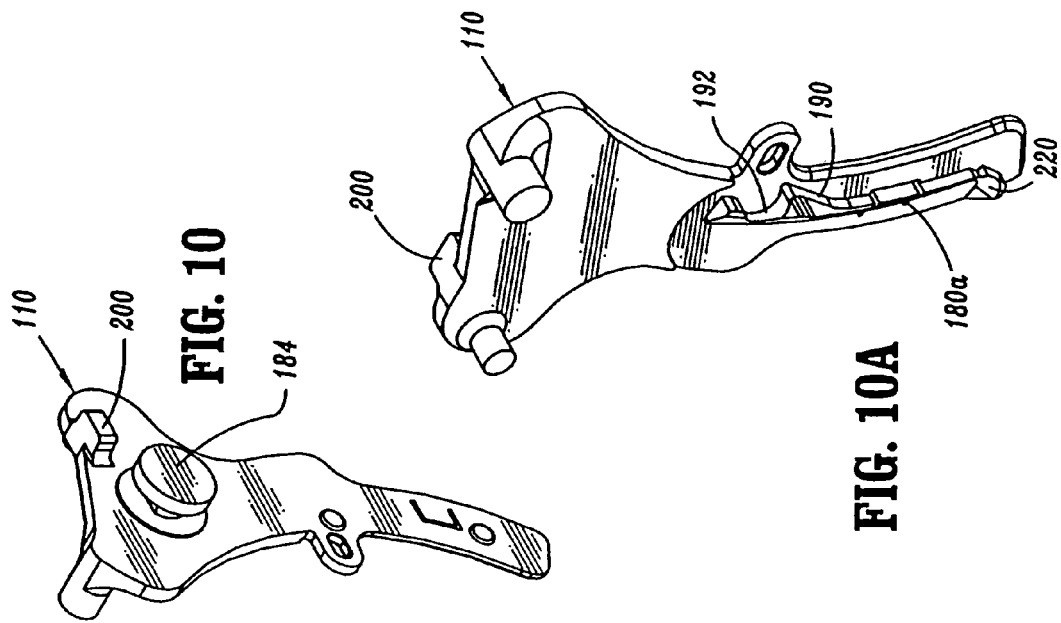
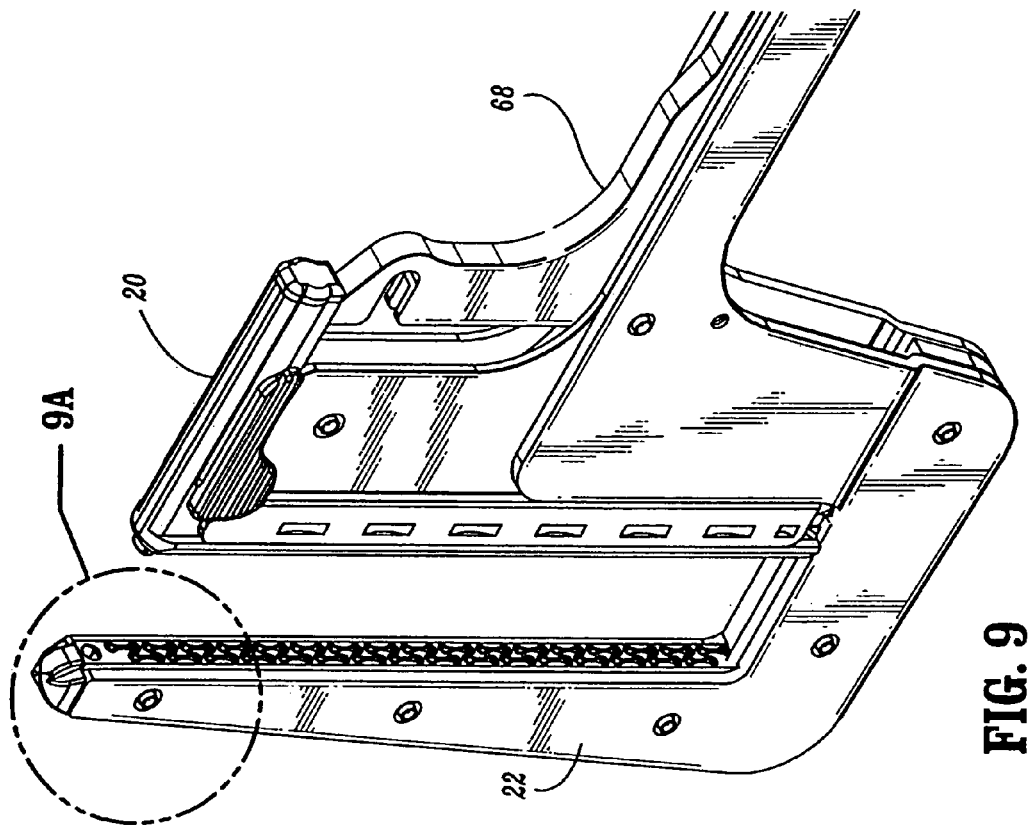

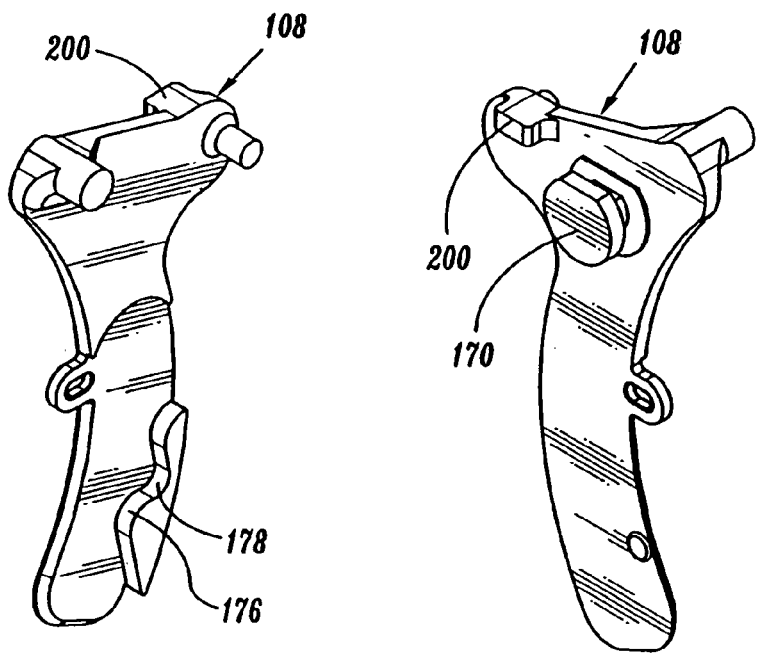
FIG. 11     FIG. 11A
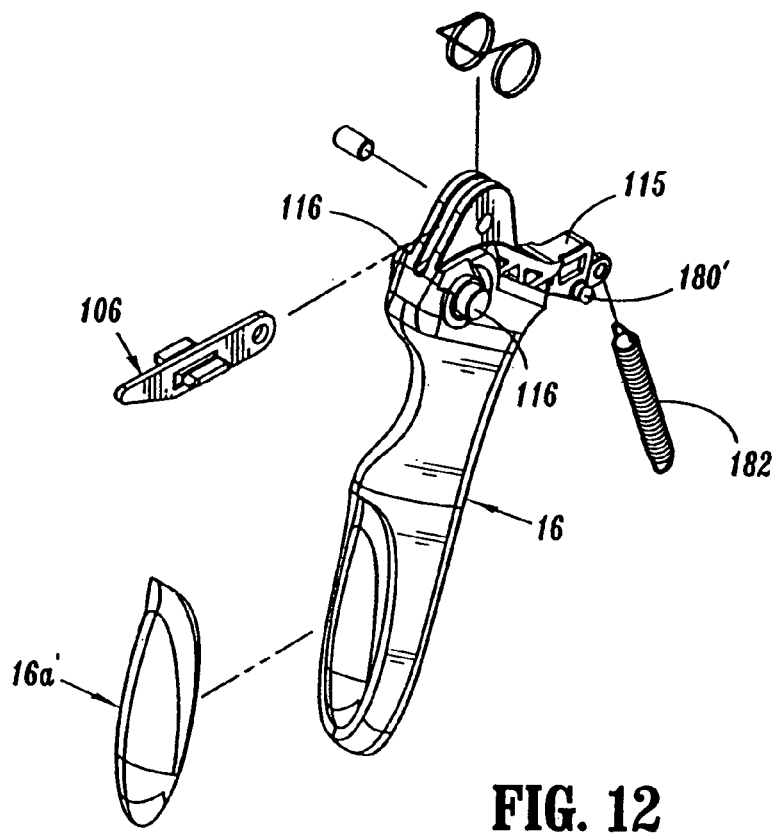
FIG. 12

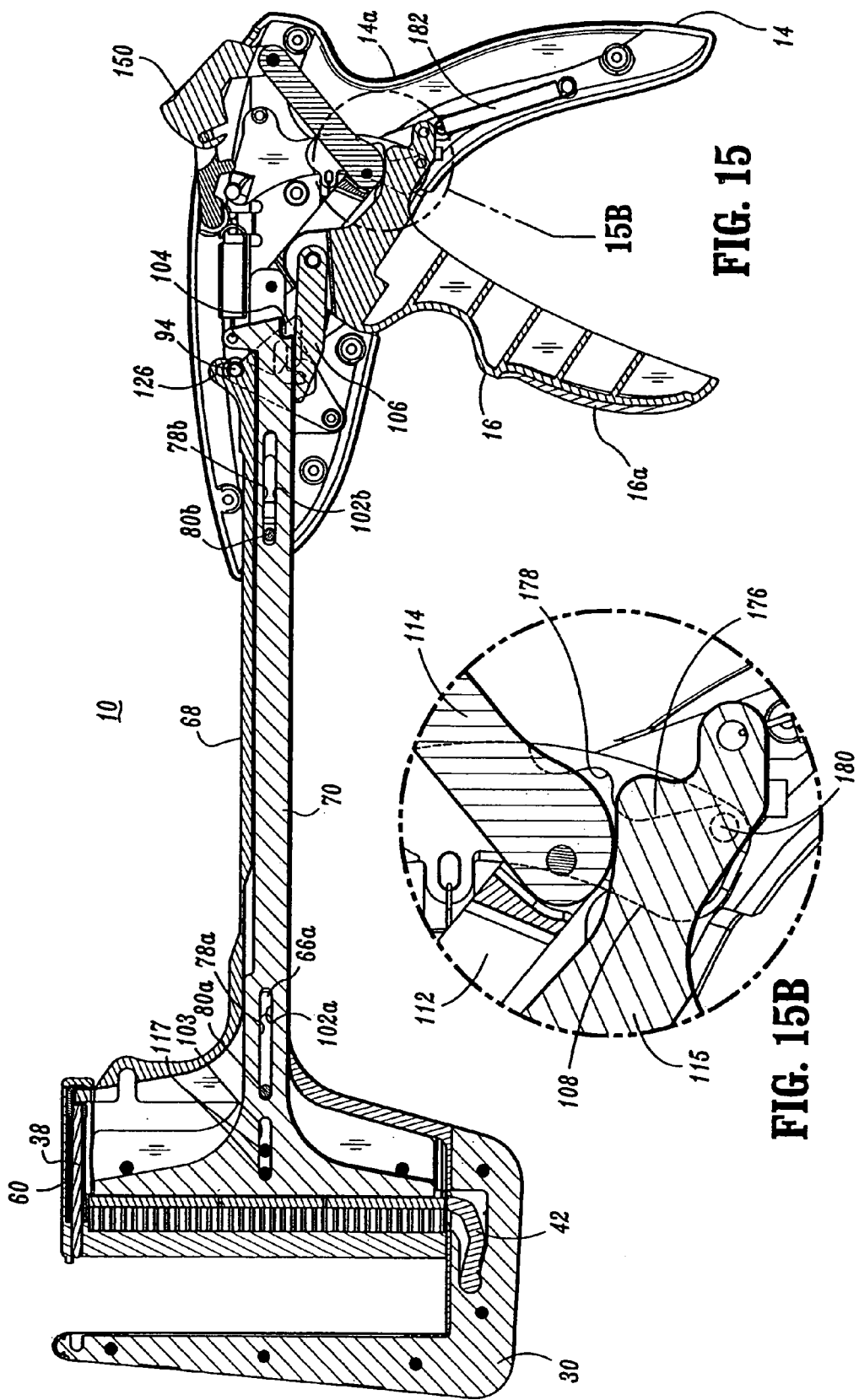

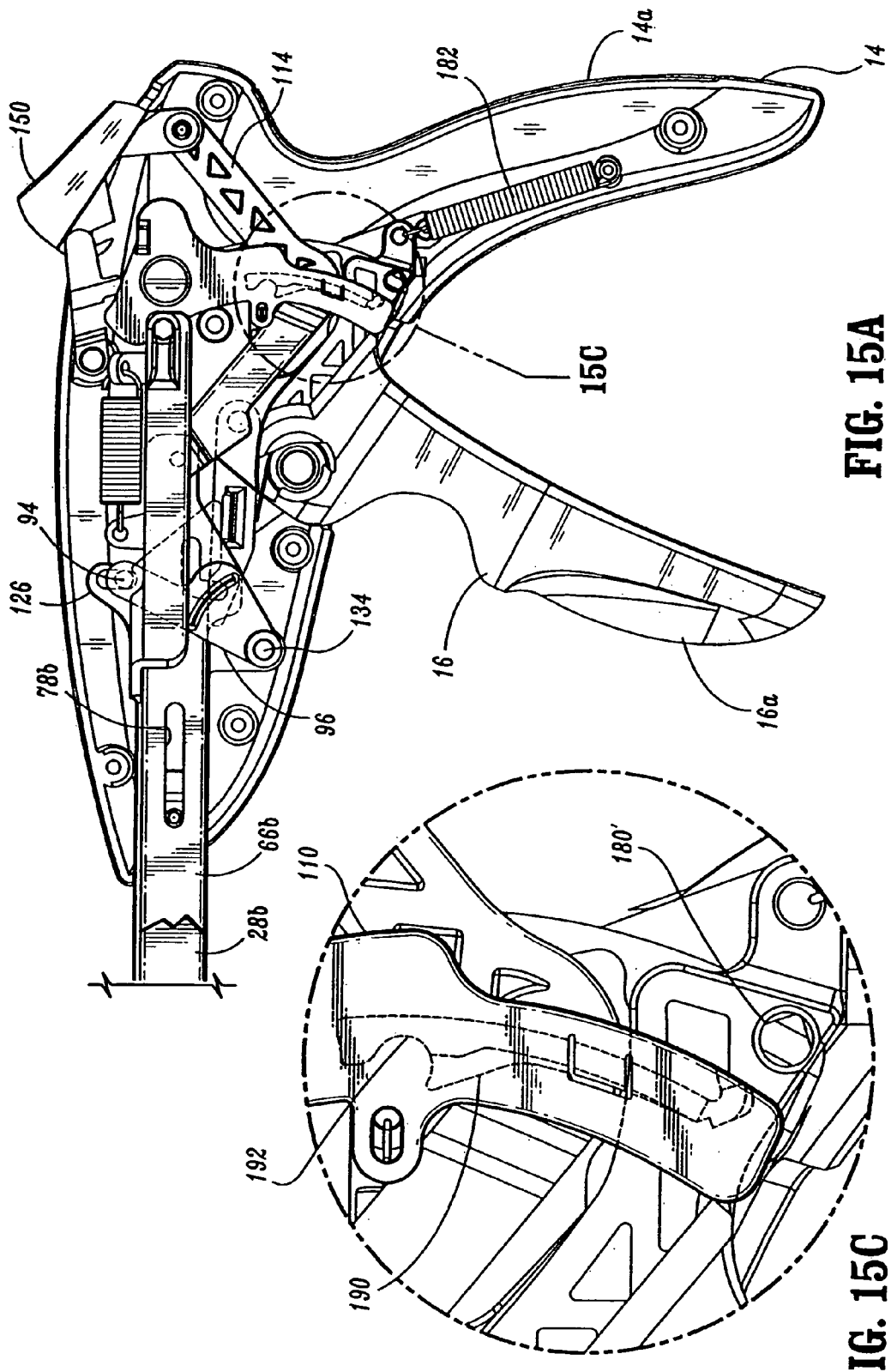

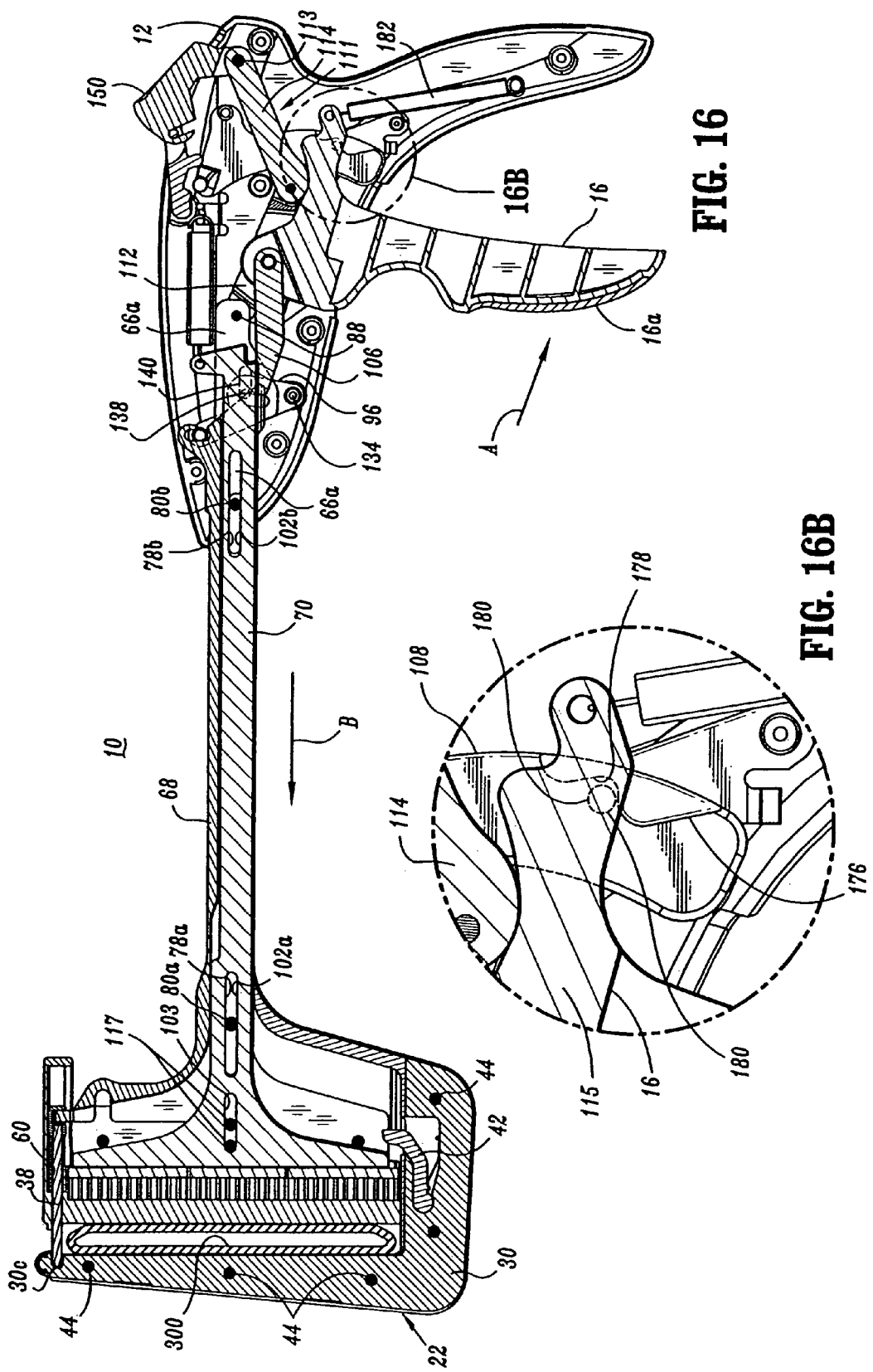

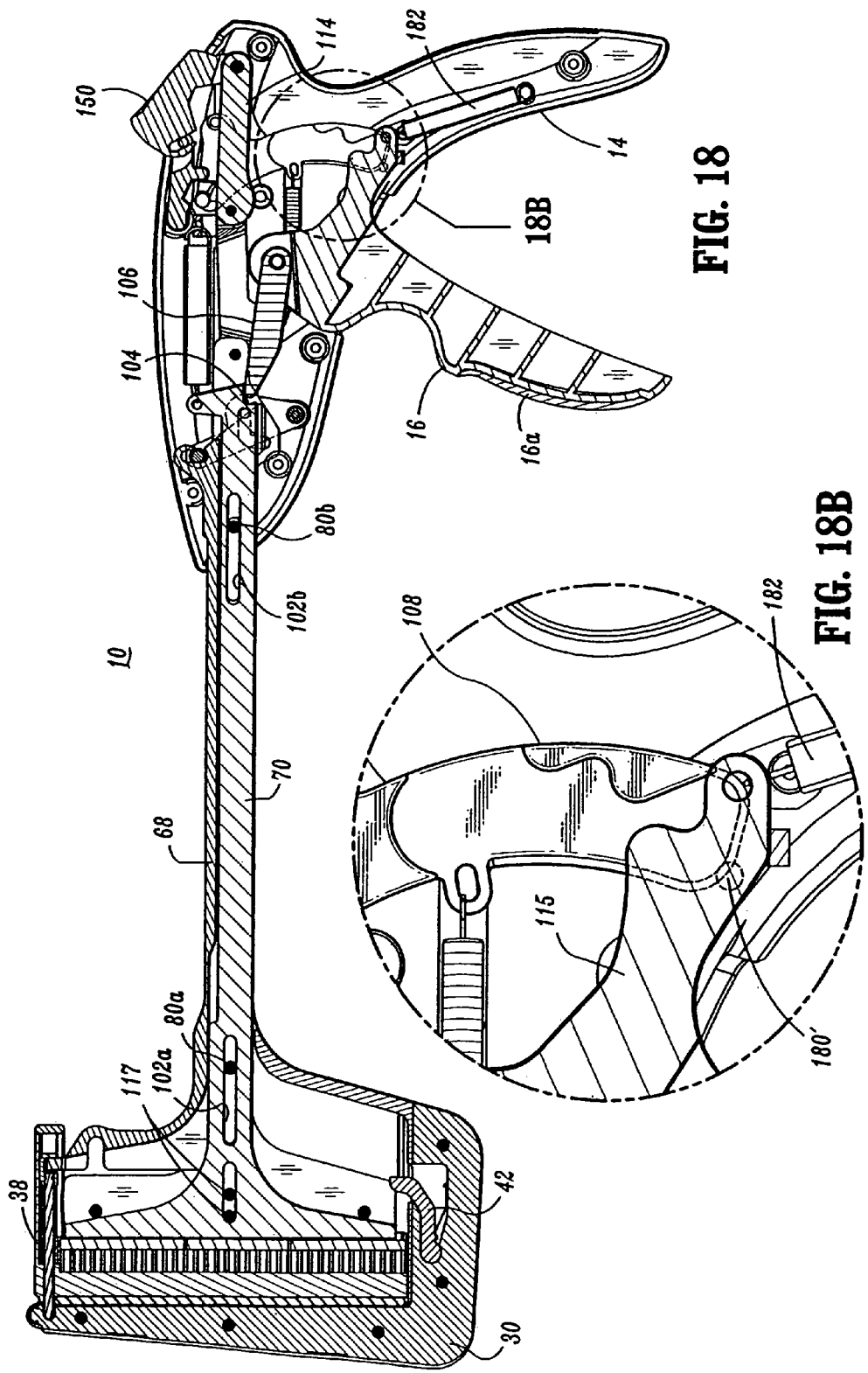

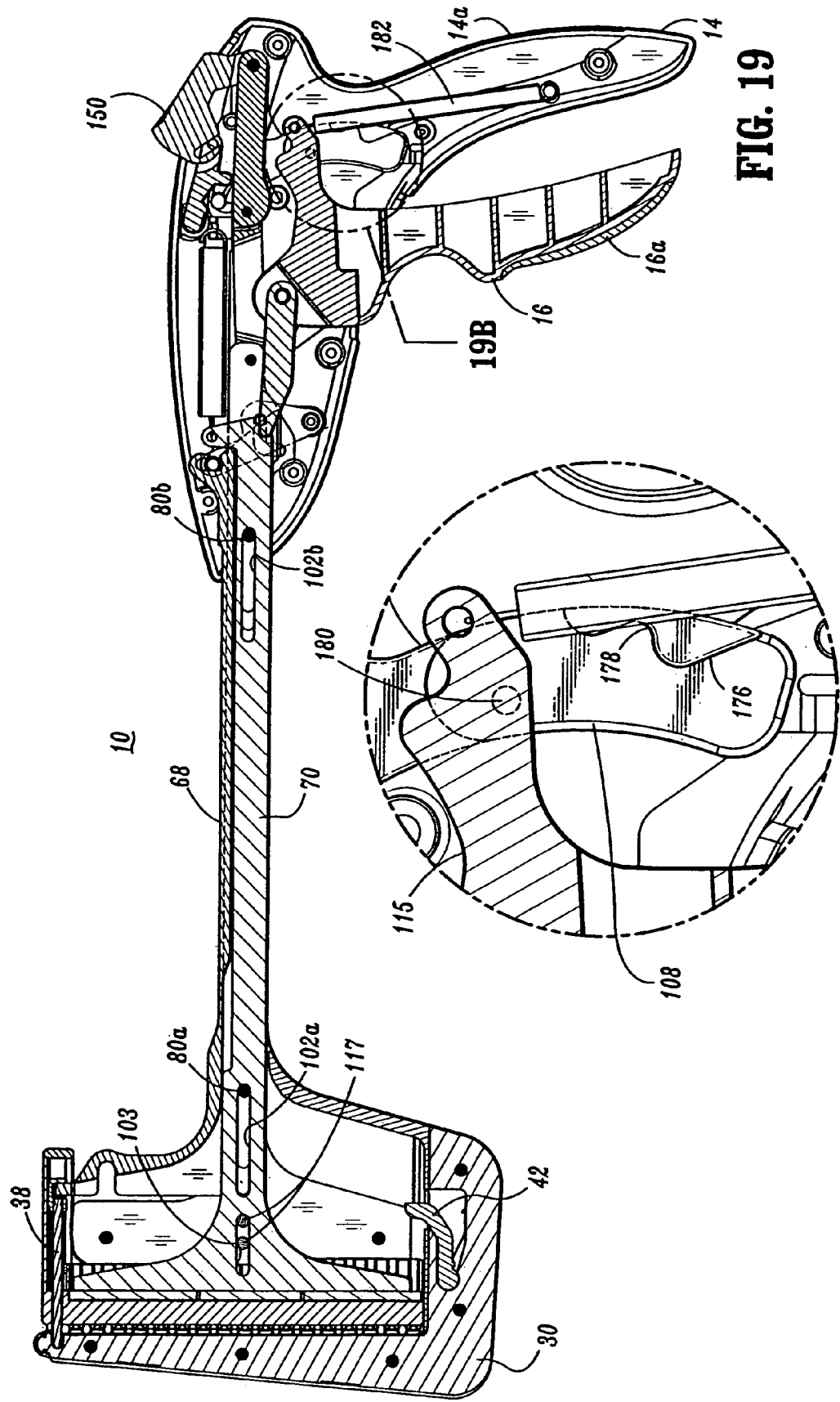

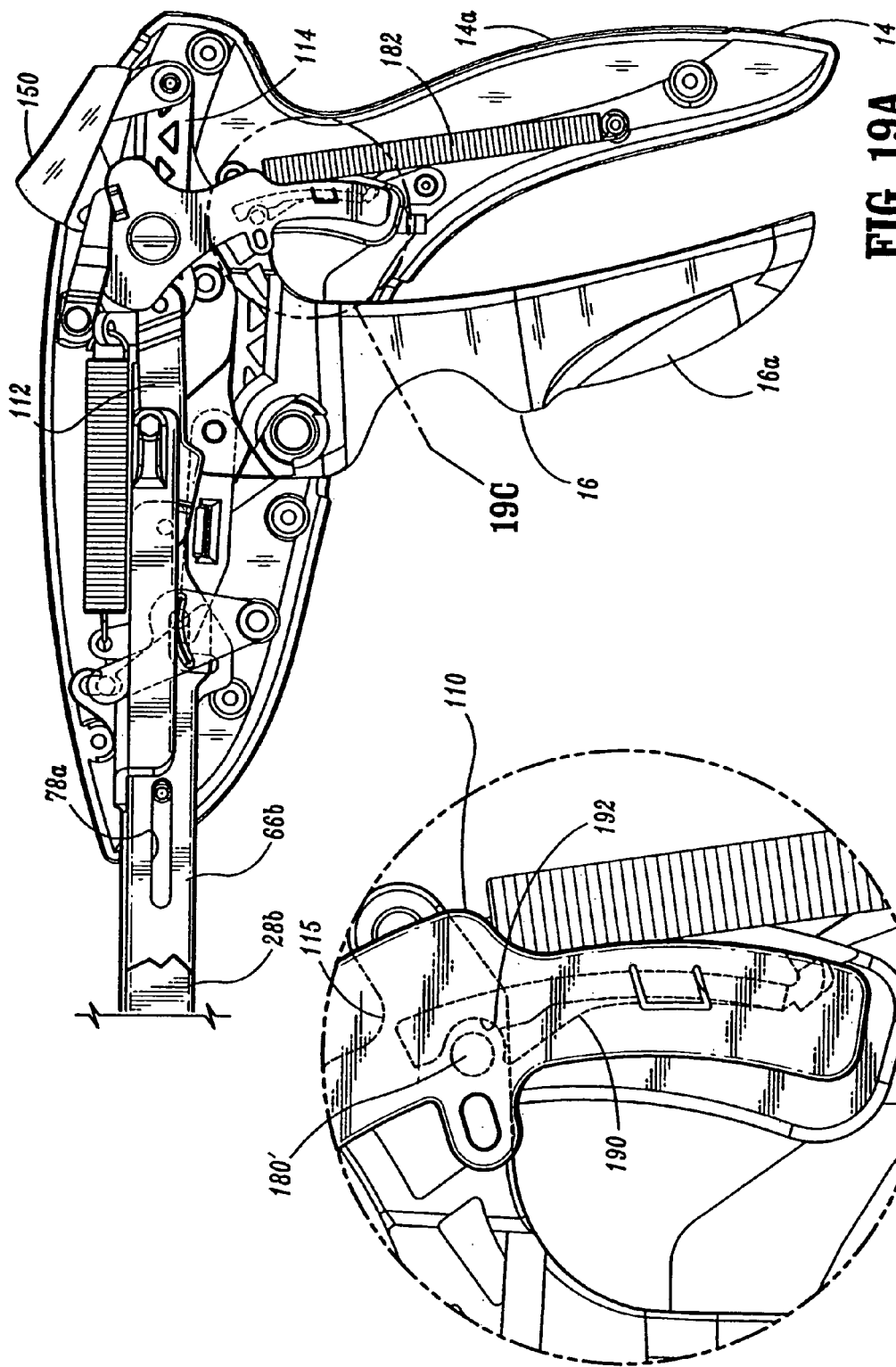

SURGICAL STAPLING DEVICE

CROSS-REFERENCE TO RELATED APPLICATIONS

This application is a continuation of U.S. patent application Ser. No. 11/436,282, filed May 18, 2006 now U.S. Pat. No. 7,275,674, which is a continuation of U.S. patent application Ser. No. 11/125,790, filed on May 10, 2005 now abandoned, which is a continuation of U.S. patent application Ser. No. 10/783,126, filed on Feb. 20, 2004, now abandoned, which is a continuation of U.S. patent application Ser. No. 09/687,815, filed on Oct. 13, 2000, now U.S. Pat. No. 6,817,508. Each of which is incorporated herein in its entirety by reference.

BACKGROUND

1. Technical Field

The present disclosure relates generally to a surgical stapling apparatus and, more specifically, to a surgical stapling apparatus having a single trigger for approximating anvil and cartridge assemblies and for ejecting an array of staples from the cartridge assembly.

2. Background of Related Art

Surgical stapling instruments used for applying parallel rows of staples through compressed living tissue are well known in the art, and are commonly used, for example, for closure of tissue or organs prior to transection, prior to resection, or in anastomoses, and for occlusion of organs in thoracic and abdominal procedures.

Typically, such surgical stapling instruments include an anvil assembly, a cartridge assembly for supporting an array of surgical staples, an approximation mechanism for approximating the anvil and cartridge assemblies, an alignment pin assembly for capturing tissue between the cartridge and anvil assemblies and for maintaining alignment between the cartridge and anvil assemblies during approximation and firing, and a firing mechanism for ejecting the surgical staples from the cartridge assembly. The approximation mechanism and the firing mechanism generally include distinct actuators for effecting approximation and firing of the staples. The alignment pin assembly can be manually operated to advance an alignment pin from the cartridge assembly into engagement with the anvil or, alternatively, the alignment pin assembly can be automatically actuated upon operation of the approximation mechanism. In instruments having a manually operated alignment pin assembly, the actuator for the alignment pin assembly is disposed at a location spaced from the handle of the instrument.

U.S. Pat. No. 4,930,503 to Pruitt discloses such a surgical stapling instrument. Pruitt's instrument includes a manually operated alignment pin assembly, an approximation mechanism including a rotatable knob actuator and a firing mechanism including a pivotable trigger. In use, a surgeon must first approximate the anvil and cartridge members by rotating the knob actuator. Next, the surgeon can advance the alignment pin assembly by advancing a knob supported on the central body portion of the instrument. Thereafter, the instrument can be fired by pivoting the trigger towards a stationary handle of the instrument.

U.S. Pat. No. 5,697,543 to Burdorff also discloses a surgical stapling instrument having an approximation mechanism, a firing mechanism and an alignment pin mechanism. The approximation and firing mechanisms each include a distinct pivotable trigger actuator. The alignment pin mechanism is operatively associated with the approximation mechanism such that upon actuation of the approximation mechanism, the alignment pin assembly is automatically advanced.

Known prior art surgical staplers are lacking in several respects. Firstly, the use of multiple actuators to effect approximation and firing of the instruments complicate the manufacture and operation of the instrument and, in most cases, require the surgeon to use two hands to hold and operate the instrument. Secondly, the instruments in which the alignment pin assembly is operatively associated with the approximation mechanism require that the instrument be approximated to advance the alignment pin assembly, despite the fact that a surgeon may prefer to advance the alignment pin assembly prior to approximation. In contrast, the instruments in which the alignment pin assembly is manually advanced typically require the surgeon to use a second hand to actuate the alignment pin assembly.

Accordingly, a continuing need exists for a surgical stapling instrument which can be operated by a surgeon with a single hand and which includes an alignment pin assembly which can be automatically or manually advanced.

SUMMARY

In accordance with the present disclosure, a surgical stapling device is provided which includes a frame having a proximal end and a distal end. A body defining a stationary handle is secured to the proximal end of the frame. A head portion including an anvil assembly and a cartridge assembly are supported on the distal end of the frame. The anvil and cartridge assemblies are movable in relation to each other between spaced and approximated positions. An approximation mechanism includes a clamp slide assembly having a distal end configured to support the cartridge assembly and a proximal end. A firing mechanism includes a thrust bar having a distal end positioned to be slidably received within the cartridge assembly. A pivotable trigger is supported on the body and is operably associated with the approximation mechanism and the firing mechanism such that the trigger is pivotable through an approximation stroke to approximate the anvil and cartridge assemblies and, subsequently, pivotable through a firing stroke to eject an array of staples from the cartridge assembly.

The presently disclosed surgical stapling device also has an alignment pin assembly which includes an alignment pin, a pin pusher and a bell crank. The alignment pin pusher is slidably supported on the frame between advanced and retracted positions. The alignment pin pusher includes a distal abutment member for engaging and advancing the alignment pin from a retracted position located within the cartridge assembly to an advanced position engaging the anvil assembly. The bell crank is operably connected to the clamp slide assembly and is releasably coupled to the pin pusher. Upon advancement of the clamp slide assembly, the bell crank is pivoted to concurrently advance the alignment pin pusher. The alignment pin pusher includes a pair of posts which extend through slots in the body. A manual engagement member or thumb button is supported on each post. The thumb button(s) can be pushed prior to approximation of the device to manually advance the alignment pin assembly into engagement with the anvil assembly. The thumb buttons are positioned on the body such that a surgeon is able to manually advance the alignment pin assembly using the same hand that actuates the pivotable trigger.

A pawl mechanism is supported in the body and includes a clamping pawl and a firing pawl. The clamping pawl functions to prevent return of the approximation mechanism after the trigger has moved through approximately three quarters of the approximation stroke. The clamping pawl also provides an audible and tactile indication that the device has been moved to the approximately three quarter approximated position. The firing pawl functions to provide an audible indication that the device is in a fire-ready position. The firing pawl also functions to lock the trigger in a compressed position after firing of the device has occurred to provide a visual indication that firing has occurred. A release button is provided to return the approximation mechanism to the retracted position at any point of operation of the device. The pivotable trigger, the release button and the thumb button are all disposed adjacent the handle portion of the device and are operable by the surgeon using a single hand.

The anvil assembly of the surgical stapling device is provided with a stiffener plate to provide increased strength to the assembly. By using the stiffener plate, the head portion profile can be reduced in size.

BRIEF DESCRIPTION OF THE DRAWINGS

Preferred embodiments of the presently disclosed surgical stapling apparatus are described herein with reference to the drawings, wherein:

FIG. 9 is an enlarged perspective view of the distal end of the surgical stapling device shown in FIG. 1;

FIG. 10 is a perspective view from one side of the firing pawl of the surgical stapling device shown in FIG. 1;

FIG. 10A is a perspective view from the other side of the firing pawl shown in FIG. 10;

FIG. 11 is a perspective view from one side of the clamping pawl of the surgical stapling device shown in FIG. 1;

FIG. 11A is a perspective view from the other side of the clamping pawl shown in FIG. 11;

FIG. 12 is a perspective view with parts separated of the trigger and firing link of the surgical stapling device shown in FIG. 1;

FIG. 15 is a side cross-sectional view of the surgical stapling device taken along section lines XX-XX of FIG. 3;

FIG. 15A is a side partial cutaway view of the handle portion of the surgical stapling device shown in FIG. 1 with a body half-section removed;

FIG. 15B is an enlarged view of the indicated area of detail shown in FIG. 15;

FIG. 15C is an enlarged view of the indicated area of detail shown in FIG. 15A;

FIG. 16 is a side cross-sectional view of the surgical stapling device shown in FIG. 1 during approximation of the anvil and cartridge assemblies;

FIG. 16B is an enlarged view of the indicated areas of detail shown in FIG. 16;

FIG. 18 is a side cross-sectional view of the surgical stapling device shown in FIG. 1 in the approximated position with the trigger in a fire-ready position;

FIG. 18B is an enlarged view of the indicated area of detail shown in FIG. 18;

FIG. 19 is a side cross-sectional view of the surgical stapling device shown in FIG. 1 after the device has been fired with the trigger in a compressed and locked position;

FIG. 19A is a side partial cutaway view of the handle portion of the surgical stapling device shown in FIG. 1 in the fired position with the left body half-section and frame removed from the handle portion of the device and the trigger in the compressed position;

FIG. 19B is an enlarged view of the indicated area of detail shown in FIG. 19;

FIG. 19C is an enlarged view of the indicated area of detail shown in FIG. 19A;

DETAILED DESCRIPTION OF PREFERRED EMBODIMENTS

Figure 1:
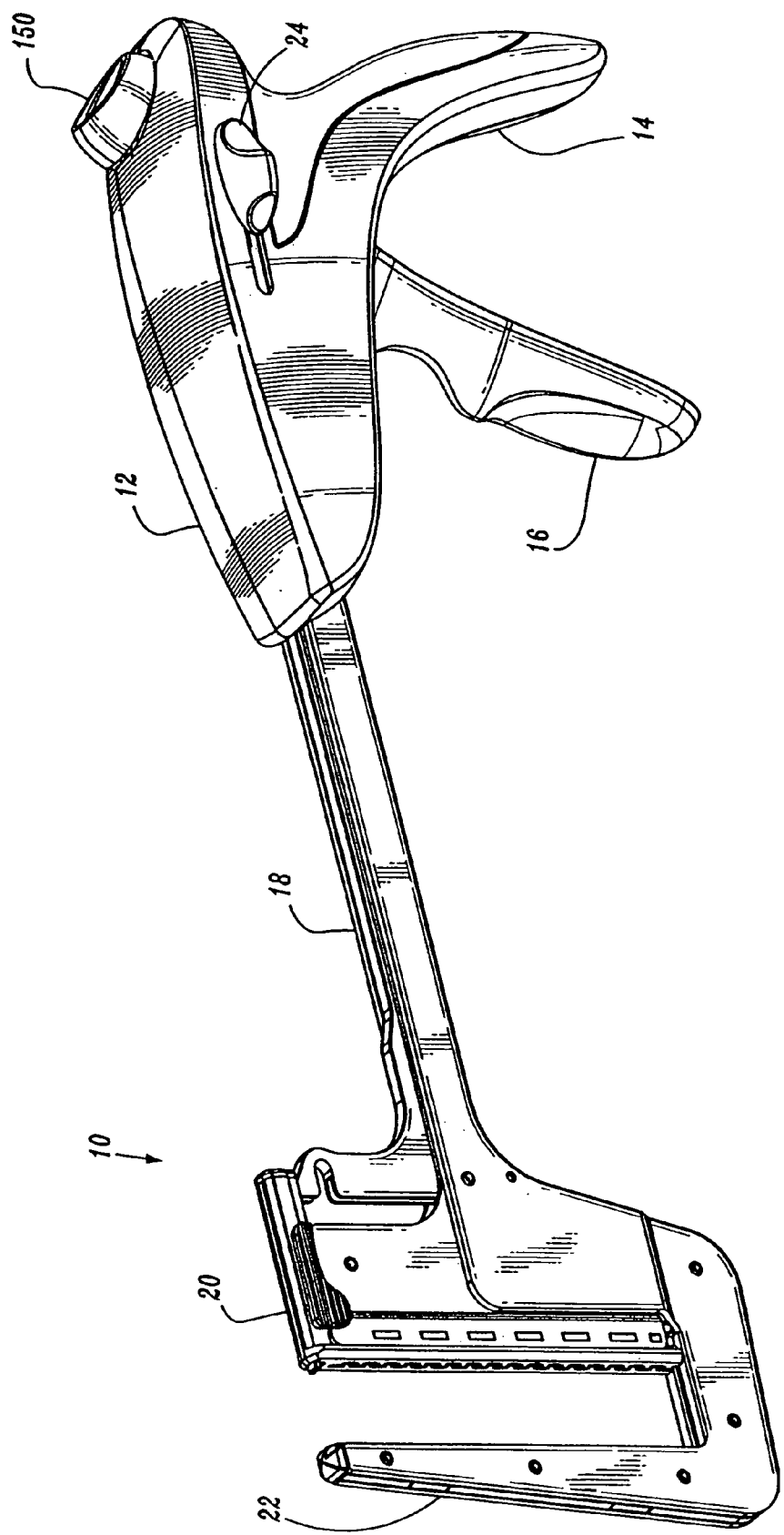
FIG. 1 is a perspective view of one embodiment of the presently disclosed surgical stapling device.

Preferred embodiments of the presently disclosed surgical stapling device will now be described in detail with reference to the drawings, wherein like reference numerals designate corresponding elements in each of the several views.

Figure 2:
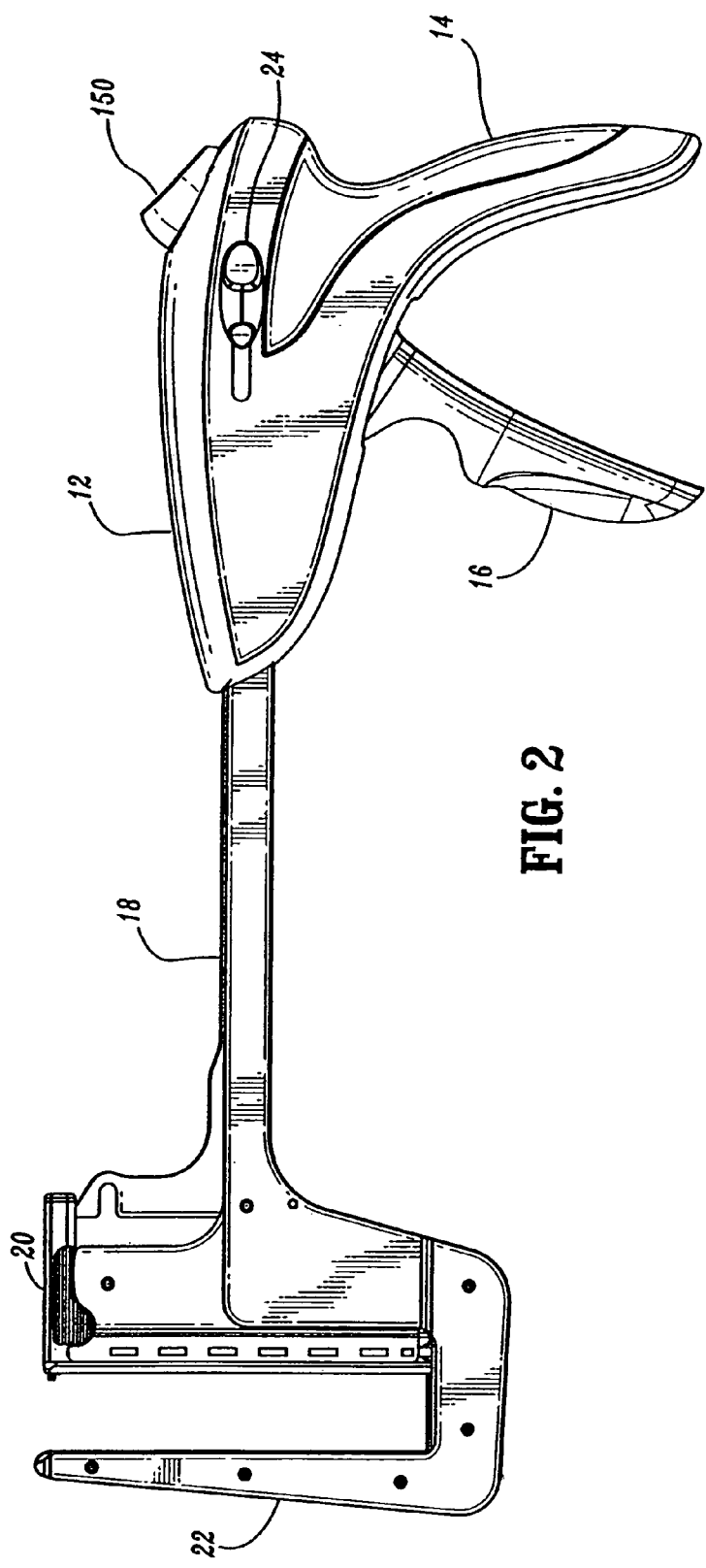
FIG. 2 is a side view of the surgical stapling device shown in FIG. 1.
Figure 3:
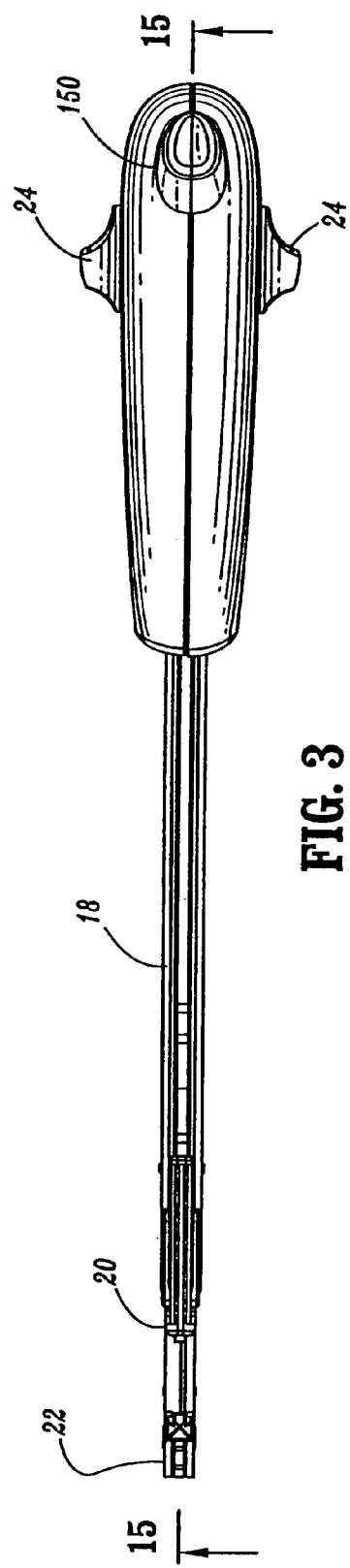
FIG. 3 is a top view of the surgical stapling device shown in FIG. 1.

The presently disclosed surgical stapling device shown generally as 10 in FIGS. 1-3 includes a body 12 defining a stationary handle 14, a pivotable trigger 16, an elongated central body portion 18, a cartridge assembly 20 and an anvil assembly 22. A manual engagement member or thumb button 24 is slidably positioned on each side of body 12. Thumb buttons 24 are movable to manually advance an alignment pin assembly in a manner to be described in detail below. A release button 150 of release mechanism 26 is positioned on the proximal end of body 12 and is depressible to allow cartridge assembly 20 to return from an approximated position disposed adjacent to anvil assembly 22 to a position spaced from anvil assembly 22 (as shown). Operation of release mechanism 26 will also be described in detail below.

Figure 4:
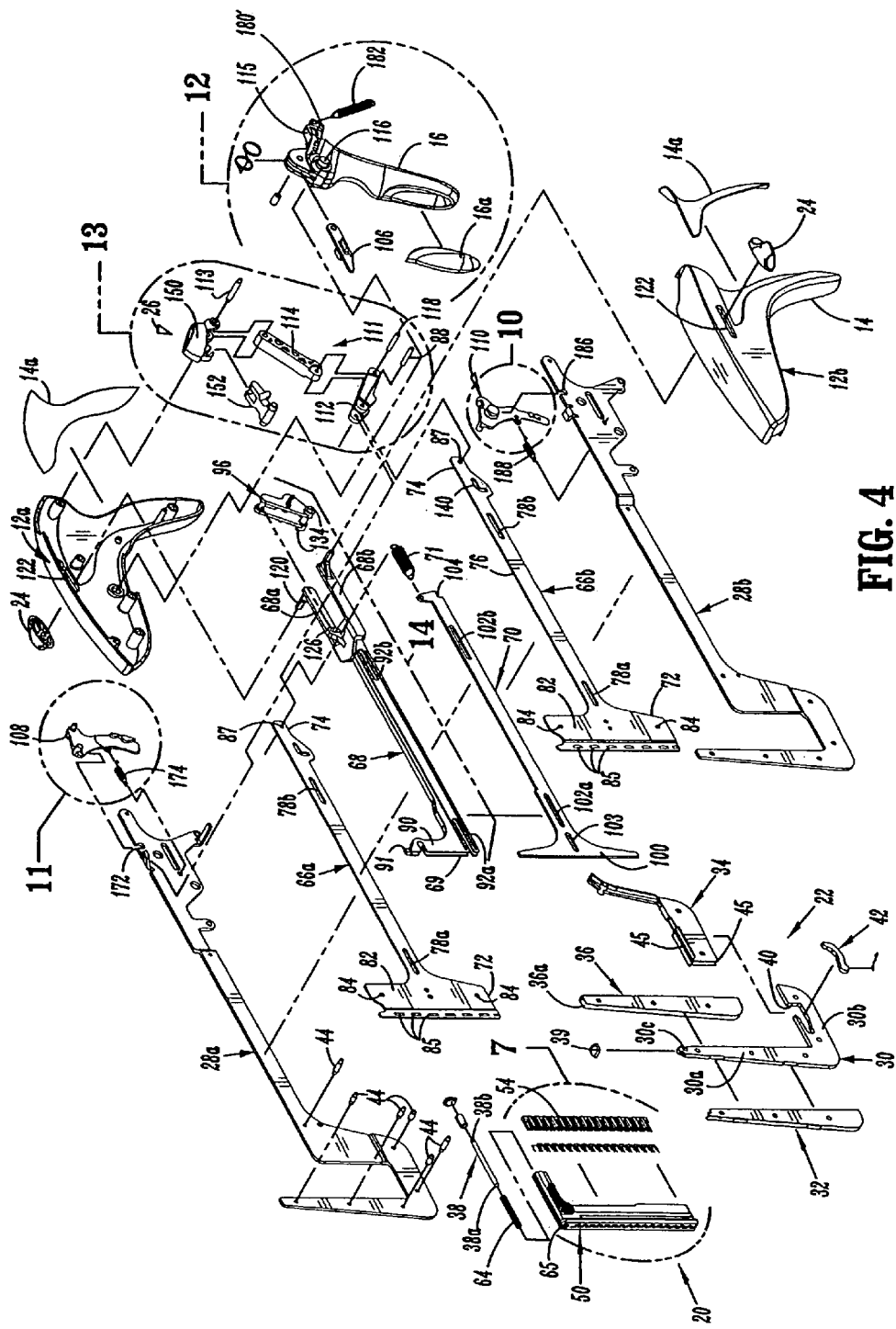
FIG. 4 is a perspective view with parts separated of the surgical stapling device shown in FIG. 1.

Referring to FIG. 4, body 12 is formed from a pair of molded half-sections 12a and 12b. Preferably, half-sections 12a and 12b are formed of plastic, although other materials including metals may be used to form the half-sections. A cushioned gripping member 14a is secured to stationary handle 14 of each half-section 12a and 12b. Gripping member 14a may be formed by injection molding a thermoplastic elastomer, such as Versaflex™ or Santaprene, to stationary handle 14. Alternately, cushioned gripping member 14a can be formed on or secured to stationary handle 14 using any known fastening technique including adhesives, screws, welding, overmolding, etc. A pair of spaced frame members 28a and 28b extend between housing half-sections 12a and 12b and anvil assembly 22. A central portion of frame members 28a and 28b form elongated central body portion 18. Preferably, frame members 28a and 28b are formed of a surgical grade metal such as stainless steel. Alternately, other suitable materials meeting the requisite strength requirements may also be used.

Figure 5:
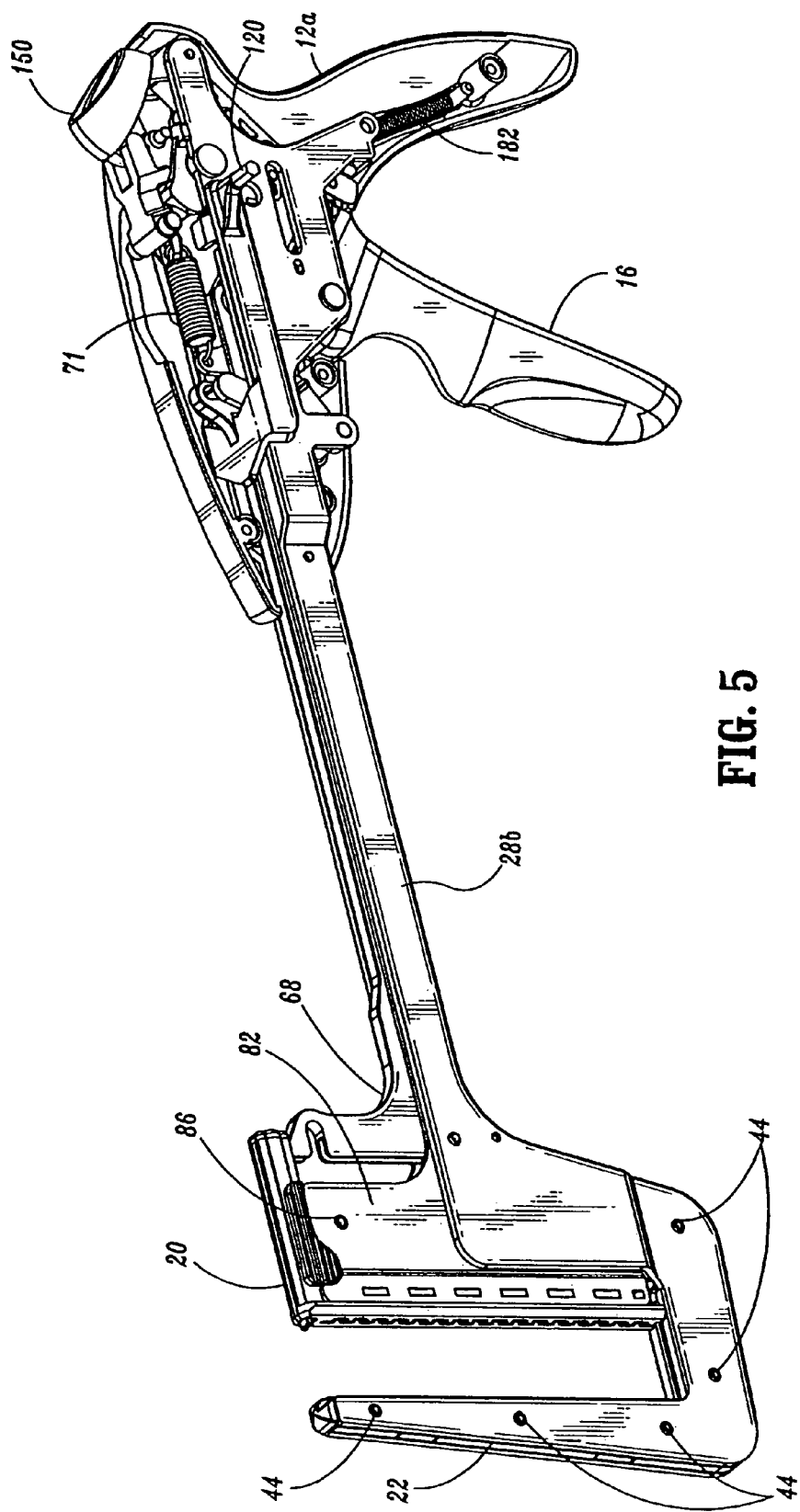
FIG. 5 is a perspective view of the surgical stapling device shown in FIG. 1 with the left body half-section removed from the handle portion of the device.
Figure 6:
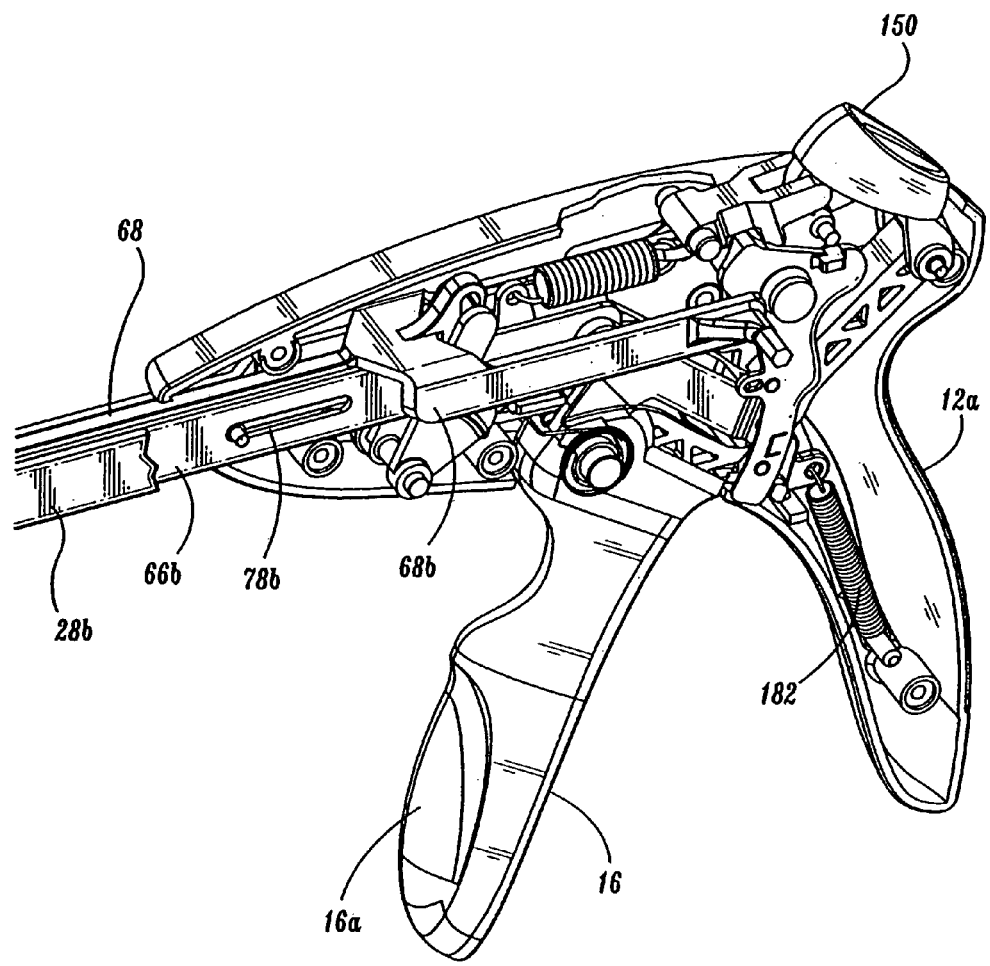
FIG. 6 is a perspective view of the handle portion of the surgical stapling device shown in FIG. 7 with a body half-section removed and a portion of the frame cutaway.
Figure 7:
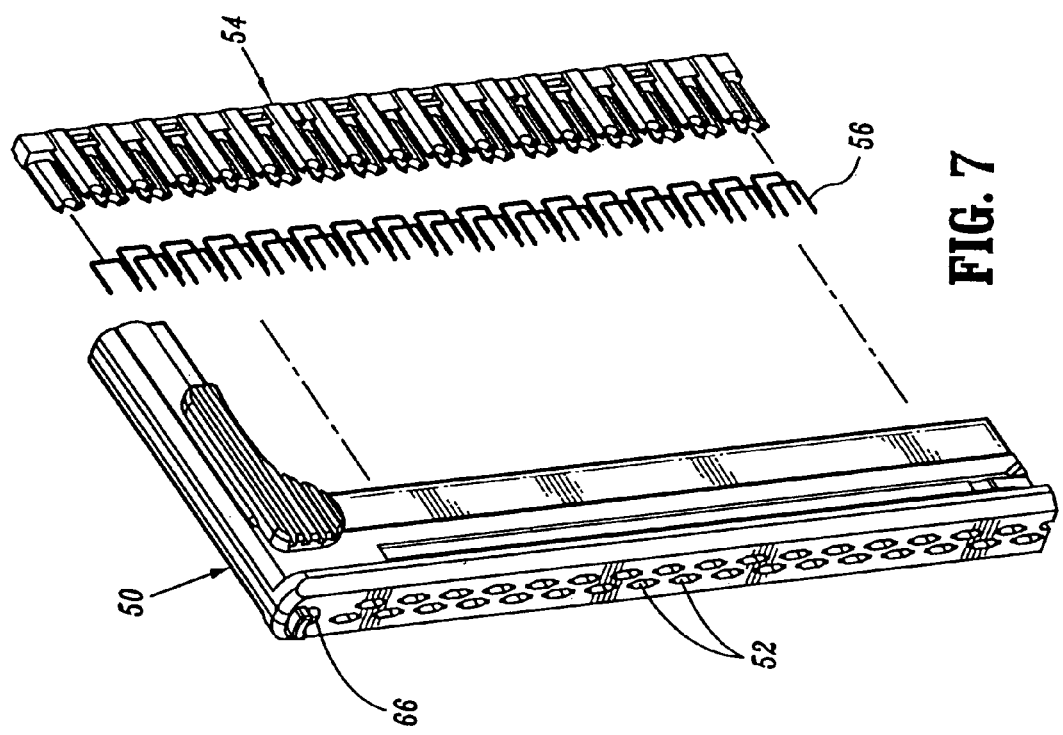
FIG. 7 is an enlarged view of the indicated area of detail shown in FIG. 4.
Figure 9A:
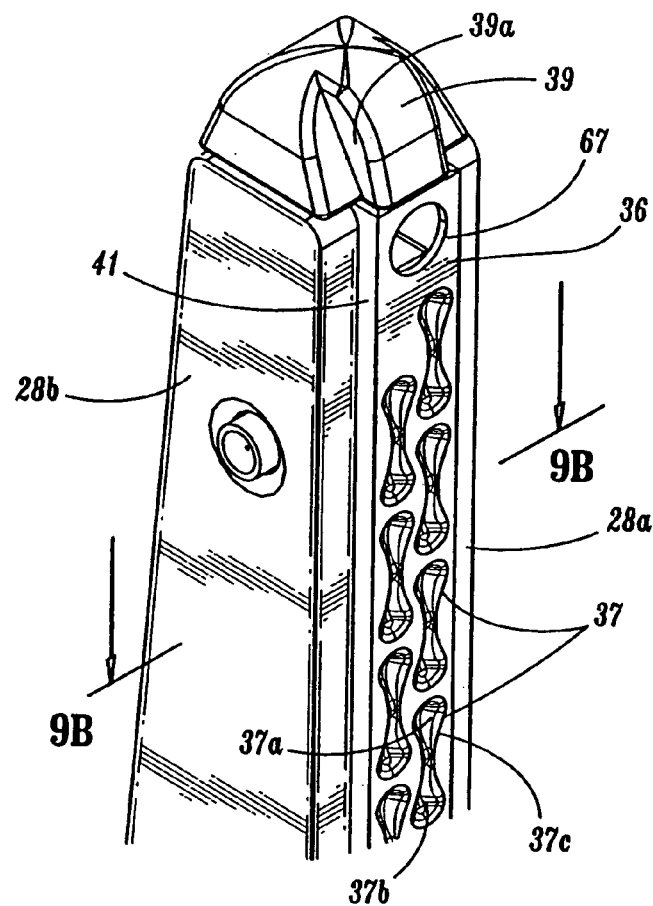
FIG. 9A is an enlarged view of the indicated area of detail shown in FIG. 9.
Figure 9B:
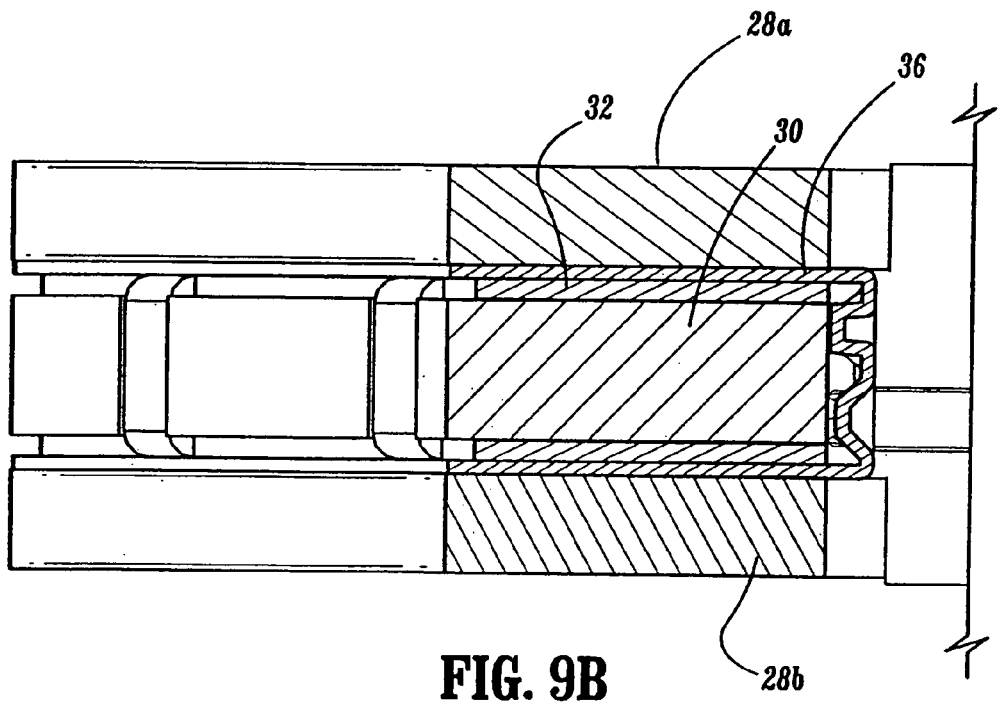
FIG. 9B is a cross-sectional view taken along section lines 9B-9B of FIG. 9A.
Figure 13:
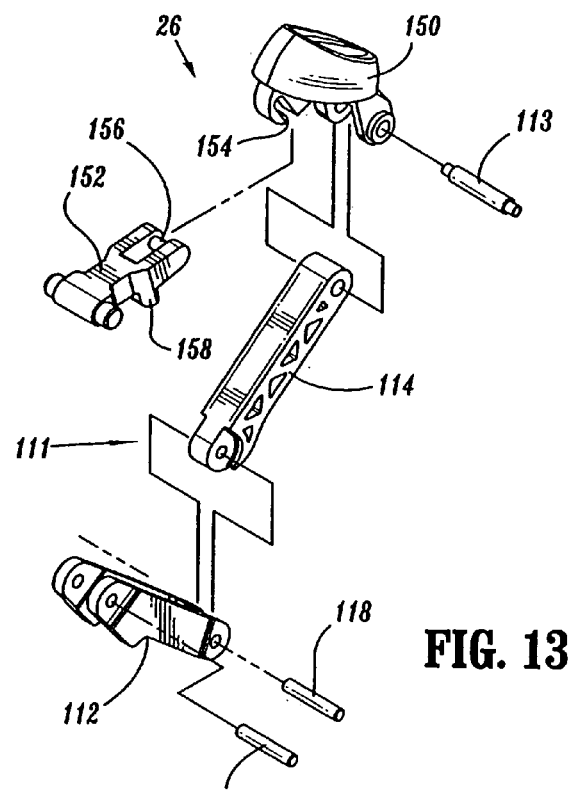
FIG. 13 is a perspective view with parts separated of the release button assembly and bi-linkage assembly of the surgical stapling device shown in FIG. 1.

Referring also to FIGS. 9-9B, anvil assembly 22 includes a stiffener plate 30, a spacer plate 32, a T-track 34, and an anvil 36. An opening 67 is formed in anvil 36 to allow passage of alignment pin 38. Stiffener plate 30 has a vertical portion 30a and a horizontal portion 30b. A notch 30c is formed in the distal end of vertical portion 30a. Notch 30c is configured to receive the tip 38a of a cartridge alignment pin 38. Horizontal portion 30b of plate 30 includes a cutout 40 dimensioned to receive an interlock member 42 which will be discussed in further detail below. In the assembled state, a distal vertical portion of frame members 28a and 28b are positioned on opposite sides of vertical portion 30a of stiffener plate 30. Spacer plate 32 includes a pair of legs which are positioned on opposite sides of stiffener plate 30 between stiffener plate 30 and anvil 36. Anvil 36 defines a channel 36a and is positioned about spacer plate 32. A cap 39 is positioned over the assembly to provide a smoother surface which is less likely to snag tissue during use. Cap 39 includes a groove 39a which defines one end of a cutting guide slot 41 formed between anvil 36 and frame member 28b. Groove 39a and cutting guide slot 41 facilitate cutting of tissue with a scalpel after device 10 has been fired. T-track 34 defines a through slot 45. Slot 45 is positioned over horizontal portion 30b of stiffener plate 30 between frame members 28a and 28b. T-track 34 is positioned about cutout 40 to define a cavity in which interlock 42 is positioned. Preferably, the anvil assembly components and frame members 28a and 28b are secured together using rivets 44 (FIG. 5). Alternately, other fastening members may be used to secure the anvil assembly components and the frame members together including screws, pins, welding, etc. Preferably, the components of anvil assembly 22 are formed of stainless steel. Alternately, other materials, including metals, having requisite strength requirements can be used to form some or all of the anvil components.

Referring to FIG. 9, anvil 36 includes a plurality of staple pockets 37 formed in the surface of the anvil. Each staple pocket 37 includes first and second staple forming cups 37a and 37b and a channeling surface 37c disposed around each of the staple forming cups. An anvil including such a staple forming pocket has been disclosed in U.S. Pat. No. 5,480,089 filed Aug. 19, 1994, the entirety of which is incorporated herein by reference.

Referring to FIGS. 4 and 7-8A, cartridge assembly 20 includes a cartridge 50 having an array of staple receiving slots 52. A staple pusher assembly 54 includes a plurality of pusher members 58. Each pusher member 58 includes a plurality of fingers 58a configured to be slidably received within a respective staple receiving slot 52. Fingers 58a are positioned behind staples 56 in slots 52 such that advancement of fingers 58a effects ejection of staples 56 from slots 52. A guide channel 60 (FIG. 15) formed in cartridge 50 is configured to slidably receive alignment pin 38. A spring 64 is positioned about pin 38 to urge alignment pin 38 to a retracted position within guide channel 60. An opening 65 formed in cartridge 50 allows alignment pin 38 to extend from guide channel 60 through anvil opening 67 (FIG.9A) into notch 30c formed in anvil assembly 22. Operation of the alignment pin mechanism for advancing alignment pin 38 will be described in detail below.

Figure 8:
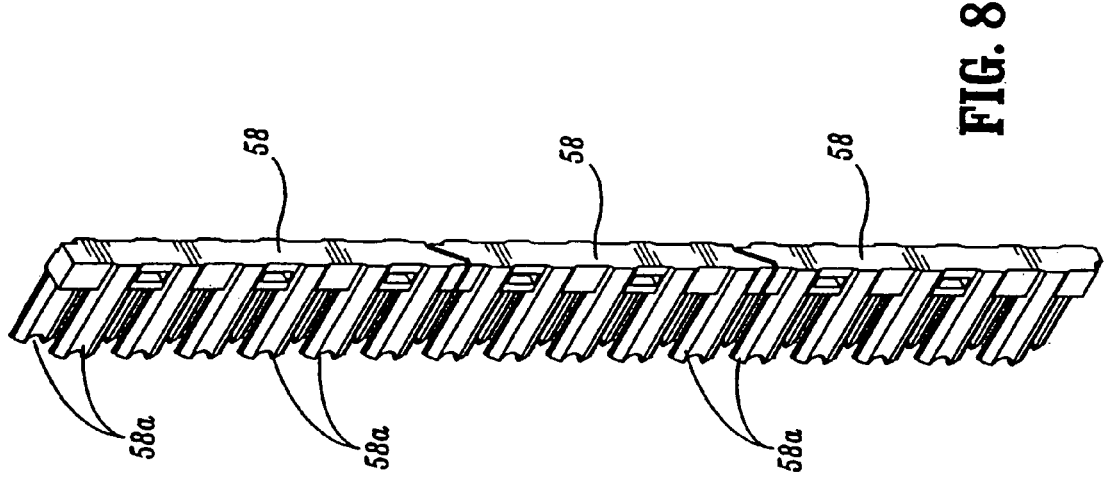
FIG. 8 is a rear perspective view of the staple pusher assembly of the surgical stapling device shown in FIG. 1.
Figure 8C:
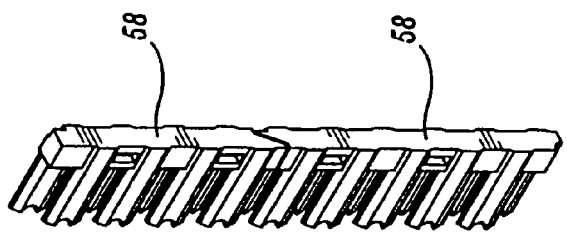
FIG. 8C is a perspective view of the staple pusher assembly shown in FIG. 8B in an assembled state.
Figure 8B:
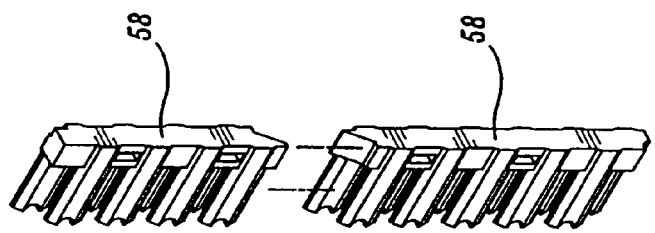
FIG. 8B is a perspective view of an alternate embodiment of the staple pusher assembly shown in FIG. 8 with parts separated.
Figure 8A:
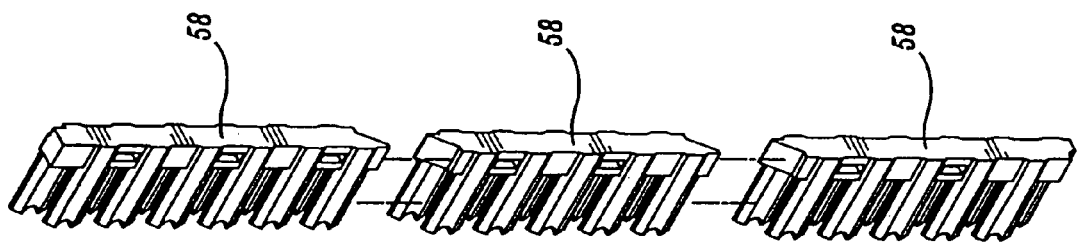
FIG. 8A is a rear perspective view of the staple pusher assembly shown in FIG. 8 with parts separated.

Referring also to FIGS. 8B and 8C, staple pusher assembly 54 includes multiple pusher members 58 which interengage to form pusher assembly 54. Pusher assembly 54 may be modified by adding or subtracting pusher members 58 to accommodate different size cartridges. For example, a pusher member 58 can be removed from the assembly such as shown in FIGS. 8B and 8C to accommodate a smaller cartridge assembly.

Referring to FIGS. 4 and 5, surgical stapling device 10 includes a pair of clamp slide members 66a and 66b, an alignment pin pusher 68 and a thrust bar 70. Clamp slide members 66a and 66b, alignment pin pusher 68 and thrust bar 70 are slidably supported between frame members 28a and 28b for movement between retracted and advanced positions in response to movement of trigger 16 through an approximation stroke and/or a firing stroke. Operation of each of the above members will be described in detail below.

Clamp slide members 66a and 66b form part of the approximation mechanism of the surgical stapling device. Each clamp slide member has a distal end 72, a proximal end 74 and an elongated body 76. Elongated body 76 includes a pair of elongated guide slots 78a and 78b. Guide slots 78a and 78b are dimensioned to slidably receive pins 80a and 80b (FIG. 15), respectively, which extend between frame members 28a and 28b. The positioning of pins 80a and 80b in guide slots 78a and 78b functions to maintain alignment between clamp slide members 66a and 66b and frame members 28a and 28b during movement between the advanced and retracted positions and to limit the extent of longitudinal movement of clamp slide members 66a and 66b, i.e., the fully advanced position of the clamp slide members is reached when the proximal end of slot 78a engages pin 80a and the fully retracted position of the clamp slide members is reached when the distal end of slot 78a engages pin 80a. Distal end 72 of each clamp slide member 66a and 66b includes a head portion 82. Each head portion 82 has a plurality of openings 84 configured to receive a fastening member 86 (FIG. 5) for securing clamp slide members 66a and 66b together in spaced relation. In the assembled state, clamp slide members 66a and 66b are spaced from each other to define an elongated channel in which pin pusher 68 and thrust bar 70 are slidably disposed. Distal end 72 of clamp slide members 66a and 66b define a cartridge support receptacle for receiving cartridge assembly 20. A series of dimples 85 on each of the clamp slide members function to frictionally retain cartridge assembly 20 within the cartridge support. Proximal end 74 of clamp slide members 66a and 66b each include a hole 87 for receiving a pin 88 of the actuation assembly which will be described in detail below.

Figure 14:
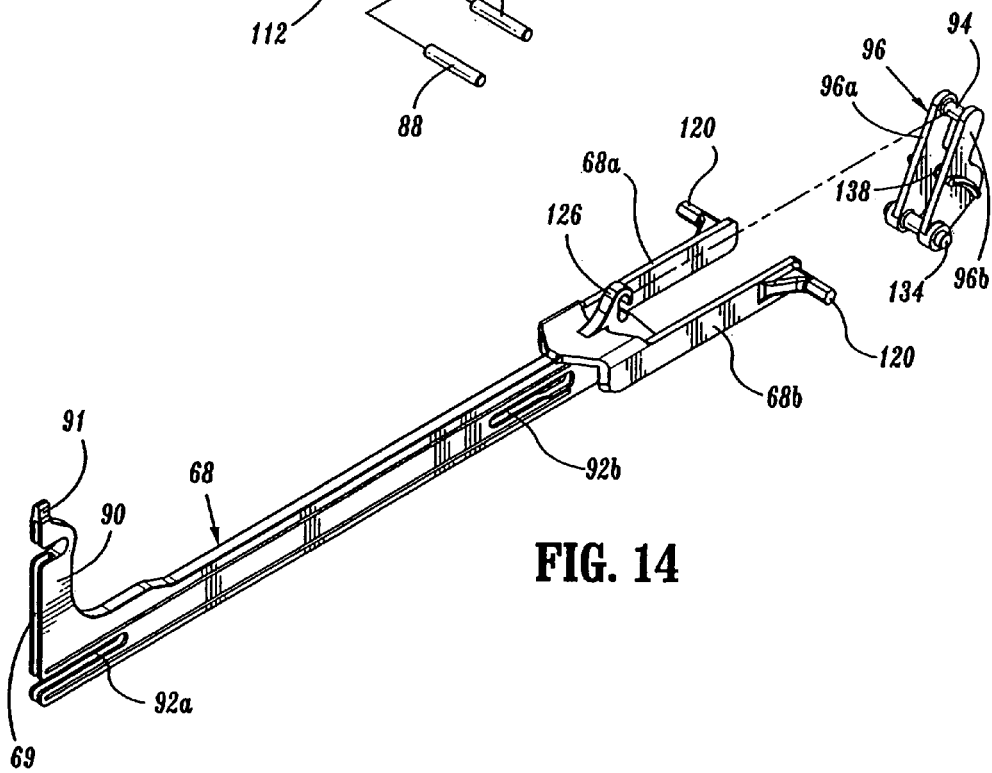
FIG. 14 is a perspective view with parts separated of the pin pusher and bell crank of the surgical stapling device shown in FIG. 1.

Referring also to FIG. 14, alignment pin pusher 68 defines a channel 69 along its length which is dimensioned to slidably receive thrust bar 70. Alignment pin pusher 68 includes a vertical portion 90 having an abutment member 91 configured to engage the proximal end 38b (FIG. 4) of alignment pin 38 such that when alignment pin pusher 68 is moved to an advanced position (in the manner described below), alignment pin 38 is advanced from within cartridge 50 through opening 65 in cartridge 50 and opening 67 in anvil 36 into notch 30c of anvil assembly 22. Alignment pin pusher 68 includes a pair of elongated slots 92a and 92b. Pins 80a and 80b (FIG. 15) extend through slots 92a and 92b, respectively, to guide alignment pin pusher 68 during movement between the advanced and retracted positions. The proximal end of alignment pin pusher 68 includes a pair of spaced legs 68a and 68b. Each leg 68a and 68b includes a radially extending post 120 which is dimensioned to extend through elongated slots 122 (FIG. 4) formed in body half-sections 12a and 12b. Thumb buttons 24 are fastened to posts 120 to facilitate manual actuation of alignment pin pusher 68. A C-clip receptacle 126 is formed on alignment pin pusher 68 and is dimensioned to releasably receive link 94 of bell crank 96. Operation of bell crank 96 and the handle actuation assembly will be described in detail below.

Referring again to FIG. 4, thrust bar 70 is slidably positioned within channel 69 defined within alignment pin pusher 68. The distal end of thrust bar 70 includes an engagement head 100 configured to engage staple pusher assembly 54. Thrust bar 70 also includes a pair of elongated slots 102a and 102b which are dimensioned to slidably receive pins 80a and 80b (FIG. 15). As discussed above with respect to clamp slide members 66a and 66b, pins 80a and 80b function not only to guide the movement of thrust bar 70 between the retracted and advanced positions, but also to define the fully advanced and fully retracted positions of thrust bar 70. As illustrated in FIG. 15, slots 102a and 102b in thrust bar 70 are longer than slots 78a and 78b formed in clamp slides 66a and 66b, respectively. The increased length of slots 102a and 102b permit thrust bar 70 to be advanced distally from the approximated position independently of clamp slides 66a and 66b through cartridge assembly 20 to eject staples from cartridge assembly 20. The proximal end of thrust bar 70 is adapted to engage a biasing member 71 which is supported in tension between frame 28a and thrust bar 70 to urge thrust bar 70 to the retracted position. The proximal end of thrust bar 70 also includes a notch 104 which is configured to receive the distal end of a firing link 106 and will be discussed in further detail below.

Referring to FIGS. 4-6, and 10-13, a handle actuation assembly includes pivotable trigger 16, a bi-linkage assembly 111 including a front link 112 and a rear link 114, bell crank 96, firing link 106 a clamping pawl 108 and a firing pawl 110. A release mechanism 26 includes a release button 150 and a release lever 152 provided within body 12.

Pivotable trigger 16 is pivotably secured between body half-sections 12a and 12b about pivot members 116 which are integrally formed on opposite sides of trigger 16. Alternately, a pivot pin can be used to pivotably support trigger 16 between the body half-sections. Trigger 16 includes a cushioned grip 16a, which may be secured to trigger 16 in the manner discussed above with respect to stationary handle 14, and a rearward extension 115 positioned beneath bi-linkage assembly 111. Rear link 114 of bi-linkage assembly 111 has a rear end pivotably secured about pivot pin 113 which extends between body members 12a and 12b and a forward end pivotably fastened to the rear end of front link 112 by pivot pin 118. It is noted that release button 150 is also pivotably secured to pivot pin 113. The forward end of front link 112 is pivotably fastened to clamp slide members 66a and 66b by pin 88. When trigger 16 is pivoted about pivot members 116, rearward extension 115 urges bi-linkage assembly 111 from a position in which the longitudinal axes of front and rear links 112 and 114 are misaligned to a position in which the axes of front and rear links 112 and 114 are substantially aligned. In the substantially aligned position, links 112 and 114 are moved to an overcenter position slightly past actual alignment. By moving the bi-linkage assembly slightly overcenter or past the aligned position, bi-linkage assembly 111 will not return to the misaligned position until engaged by the release mechanism 26. Since the rear end of rear link 114 is fastened within body 12, as bi-linkage assembly 111 is moved from the misaligned to the aligned position, front link 112 is advanced distally to advance clamp slide members 66a and 66b distally. Advancement of clamp slide members 66a and 66b effects corresponding advancement of cartridge assembly 20 to effect approximation of anvil and cartridge assemblies 22 and 20, respectively.

Referring to FIGS. 4 and 15, thrust bar 70 includes a forward elongated slot 103. Rivets 117, which extend between clamp slide members 66a and 66b, also extend through slot 103. When clamp slide members 66a and 66b are advanced from a retracted position to an advanced position, rivets 117 engage the forward end of slot 103 to advance thrust bar 70 concurrently with clamp slide members 66a and 66b. As illustrated in FIG. 15, slot 103 is of a length to allow thrust bar 70 to advance distally beyond the approximated position independently of clamp slide members 66a and 66b.

Referring to FIGS. 4 and 14, bell crank 96 is pivotably secured between frame members 28a and 28b by pivot member 134. As discussed above, link 94 of bell crank 96 is releasably positioned within C-clip 126 of alignment pin pusher 68. Bell crank 96 includes a pair of spaced sidewalls 96a and 96b. Each sidewall includes an inwardly extending cam member 138 which is configured to be received within a cam slot 140 formed in the proximal end of clamp slides 66a and 66b. As clamp slides 66a and 66b are advanced distally, the walls defining cam slots 140 engage cam members 138 to pivot bell crank 96 about pivot member 134. When bell crank 96 is pivoted, post 94 urges pin pusher 68 distally to advance abutment member 91 through guide channel 60 to advance alignment pin 38 into engagement with anvil assembly 22.

Cam slots 140 are configured to quickly pivot bell crank 96 during the initial advancement of clamp slides 66a and 66b such as to quickly advance alignment pin pusher 68 and alignment pin 38 during the initial stage of approximation.

Referring again to FIGS. 4 and 13, release mechanism 26 includes release button 150 and release lever 152. As discussed above, release button 150 includes a rear end which is pivotably secured to pivot pin 113. Pivot pin 113 is secured between body members 12a and 12b. The forward end of release button 150 includes a slot 154 dimensioned to slidably receive a rod 156 formed on a rear end of release lever 152. The forward end of release lever 152 is pivotably secured between body half-sections 12a and 12b. An engagement member 158 projects downwardly from the bottom of release lever 152 and is positioned to abut bi-linkage assembly 111 when release button 150 is depressed to urge bi-linkage assembly 111 from the substantially aligned overcenter position to the misaligned position.

Referring to FIGS. 4 and 10-12, surgical stapling apparatus 10 includes a pawl assembly including clamping pawl 108 and firing pawl 110. Clamping pawl 108 is pivotably secured about pivot member 170 in semi-circular slot 172 (FIG. 4) in frame 28a. A spring 174 is secured between clamping pawl 108 and frame 28a to urge clamping pawl 108 to rotate in a clockwise direction as viewed in FIG. 4. Clamping pawl 108 includes a cam surface 176 having a recess 178 positioned to engage cam member 180 (FIG. 16B) formed on extension 115 of trigger 16. When cam member 180 on trigger 16 is positioned in recess 178 of cam surface 176 (this occurs after the clamp slides 66a and 66b have been moved through approximately three quarters of the approximation stroke), trigger 16 is prevented from being returned by spring 182 to a non-compressed position. Thus, the cartridge assembly 20 and the anvil assembly 22 are maintained in a three quarter approximated position even when trigger 16 is released by the surgeon. Firing pawl 110 is pivotably secured about pivot member 184 in semi-circular slot 186 (FIG. 4) formed in frame 28b. Spring 188 is secured between firing pawl 110 and frame 28b to urge the firing pawl in a clockwise direction as viewed in FIG. 4. Firing pawl 110 includes a cam surface 190 having a recess 192 for engaging a cam member 180' formed on a side of extension 115 of trigger 16 opposite cam member 180. During movement of trigger 16 through the firing stroke, cam member 180' is moved into recess 192 to lock trigger 16 in a compressed position after firing has been completed. This provides an audible and visual indication to the surgeon that firing has been completed. Additional operational details of the pawl assembly will be described in the following description of the operation of surgical stapling device 10.

Operation of the surgical stapling device will now be described in detail with reference to FIGS. 15-20A. It is noted that the movements of the various components will be described from the vantage point of one viewing the instrument as positioned in the referenced FIG.

FIGS. 15-15C illustrate surgical stapling device 10 prior to use. As illustrated, cartridge assembly 20 and anvil assembly 22 are in spaced relation, trigger 16 is in the non-compressed position, and clamp slides 66a and 66b and thrust bar 70 are in the retracted position (note pins 80a and 80b are positioned in the forward end of slots 78a and 78b of clamp slides 66a and 66b and slots 102a and 102b of thrust bar 70). When thrust bar 70 is in the retracted position, the forward end of firing link 106 is positioned forwardly of notch 104 in thrust bar 70. Since link 106 cannot engage notch 104, device 10 cannot be fired in this position. Alignment pin pusher 68 and alignment pin 38 are also in the retracted position with post 94 of bell crank 96 engaged in C-clip 126 of alignment pin pusher 68. At this point, a surgeon could manually advance alignment pin pusher 68 and alignment pin 38 by pushing thumb button(s) 24 (FIG. 1) towards the forward end of slots 122 formed in body halves 12a and 12b. This operation would disengage post 94 from C-clip 126.

Figures 16A, 16C:
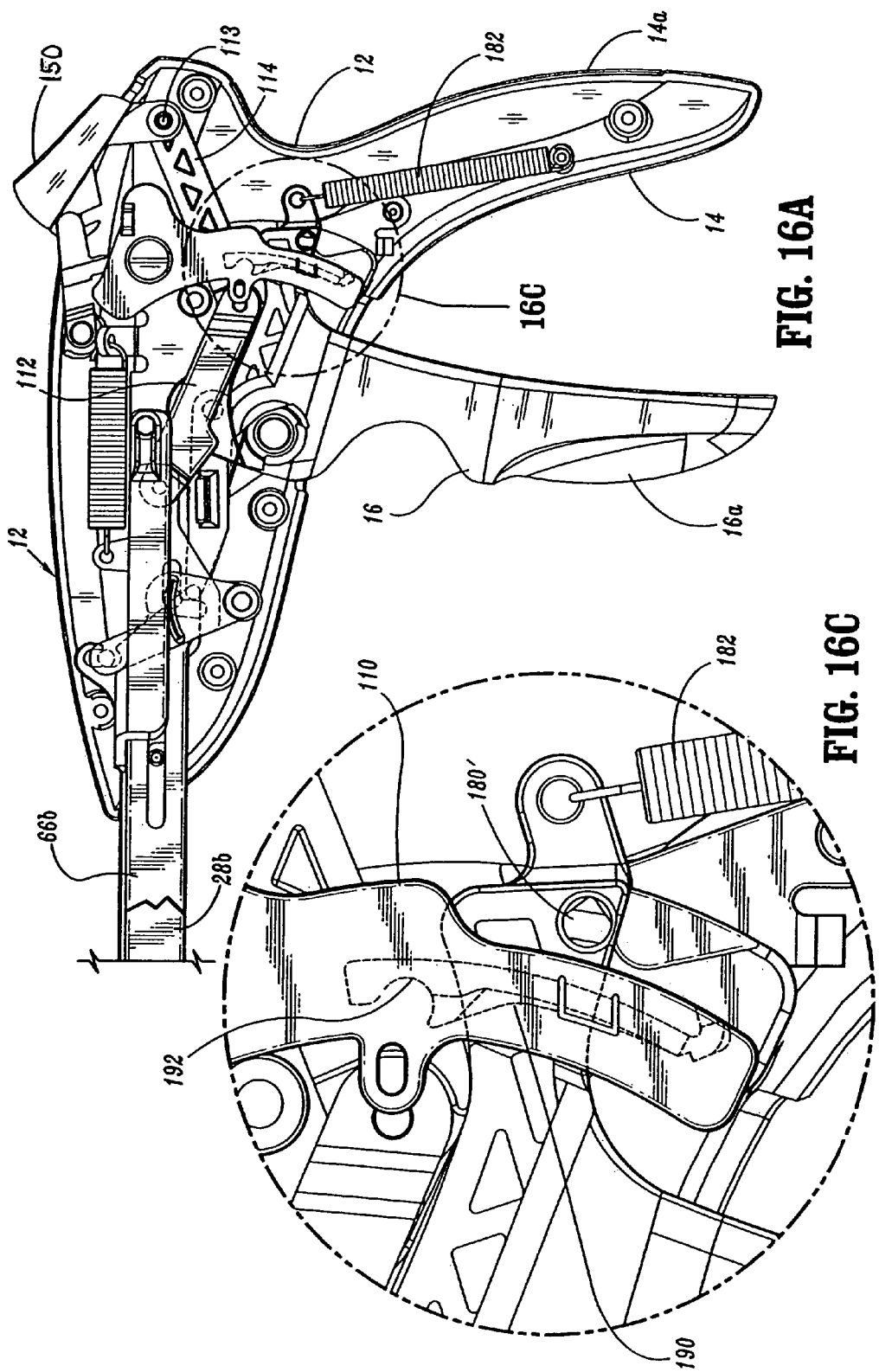
FIG. 16A is a side partial cutaway view of the handle portion of the surgical stapling device shown in FIG. 1 during approximation of the anvil and cartridge assemblies with the left body half-section removed from the handle portion of the device.
FIG. 16C is an enlarged view of the indicated area of detail shown in FIG. 16A.

FIGS. 16-16C illustrate surgical stapling device 10 during the approximation stroke of trigger 16. As illustrated, trigger 16 is moved in the direction indicated by arrow "A" to move extension 115 of trigger 16 in a direction to urge bi-linkage assembly 111 from the misaligned position towards the substantially aligned position. Because rear link 114 is secured to body 12 about pin 113, front link 112 extends forwardly. Front link 112 is secured to clamp slides 66a and 66b by pin 88. As front link 112 is extended forwardly, clamp slides 66a and 66b are advanced in the direction indicated by arrow "B" from the retracted position towards the advanced or approximated position. Note the position of pins 80a and 80b in slots 78a and 78b and 102a and 102b. As discussed above, rivets 117 extend between clamp slides 66a and 66b through 103 formed in thrust bar 70. As clamp slides 66a and 66b are advanced, rivet 88 engages the forward end of slot 103 formed in thrust bar 70 to simultaneously advance thrust bar 70. As clamp slides 66a and 66b are advanced, engagement between cam slots 140 and cam member 138 pivots bell crank 96 about pivot member 134 to urge pin pusher 68 distally to advance alignment pin 38 into notch 30c of anvil assembly 22.

Referring to FIG. 16B, as trigger 16 is pivoted in the direction indicated by arrow "A", cam member 180 on extension 115 of trigger 16 rides up cam surface 176 against the bias of spring 174 (FIG. 4). When trigger 16 is pivoted to advance clamp slide members 66c and 66b through approximately three quarters of the approximation stroke, cam member 180 snaps into cam recess 178 to provide an audible and a tactile indication that approximately three quarter approximation has been reached. At this point, the positioning of cam member 180 in cam recess 178 prevents spring 182 from returning trigger 16 to the non-compressed position without activating release mechanism 26. Operation of the release mechanism will be discussed below.

Figures 17, 17B:
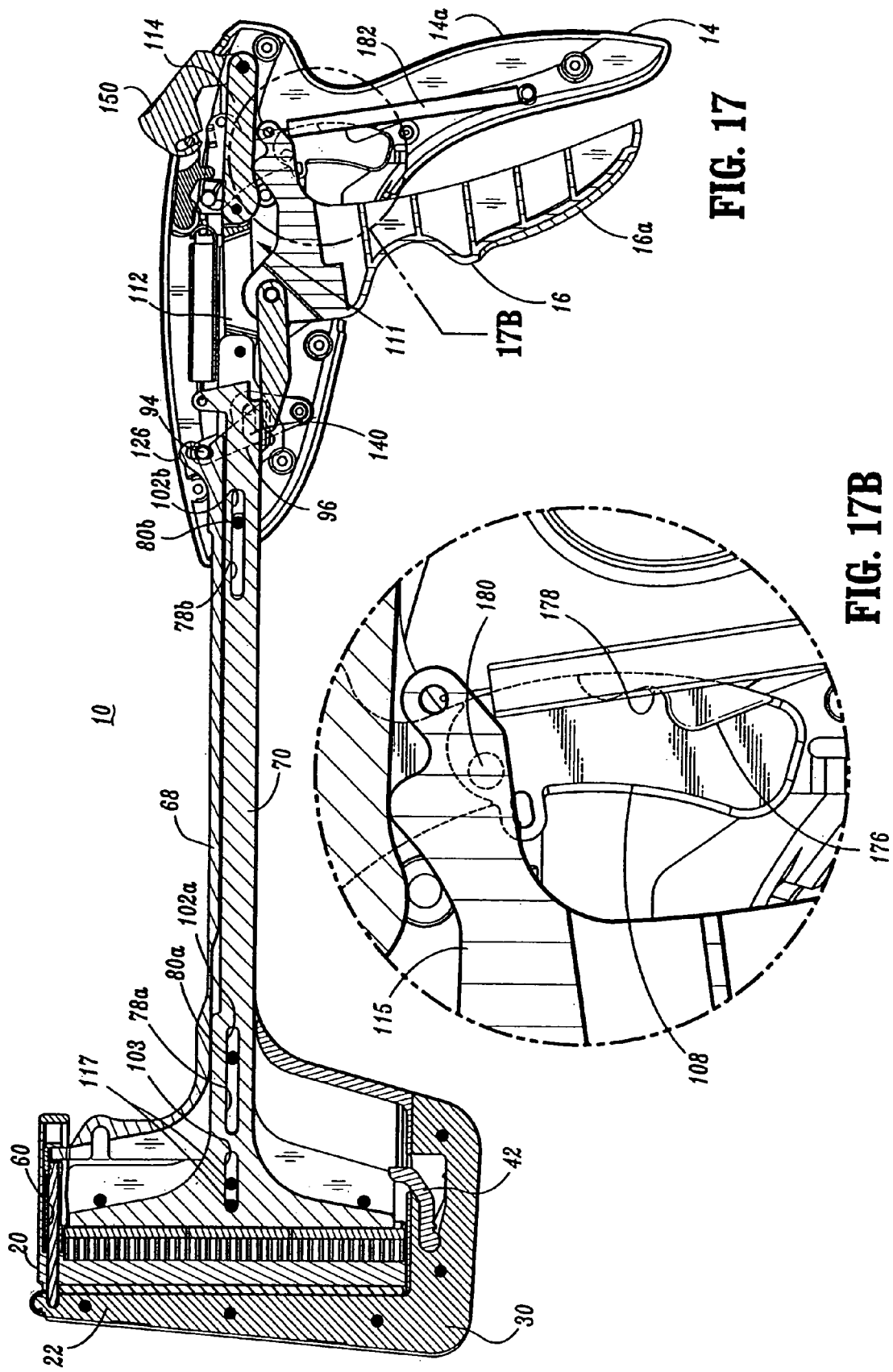
FIG. 17 is a side cross-sectional view of the surgical stapling device shown in FIG. 1 in the approximated position with the trigger in the compressed position.
FIG. 17B is an enlarged view of the indicated area of detail shown in FIG. 17.
Figures 17A, 17C:
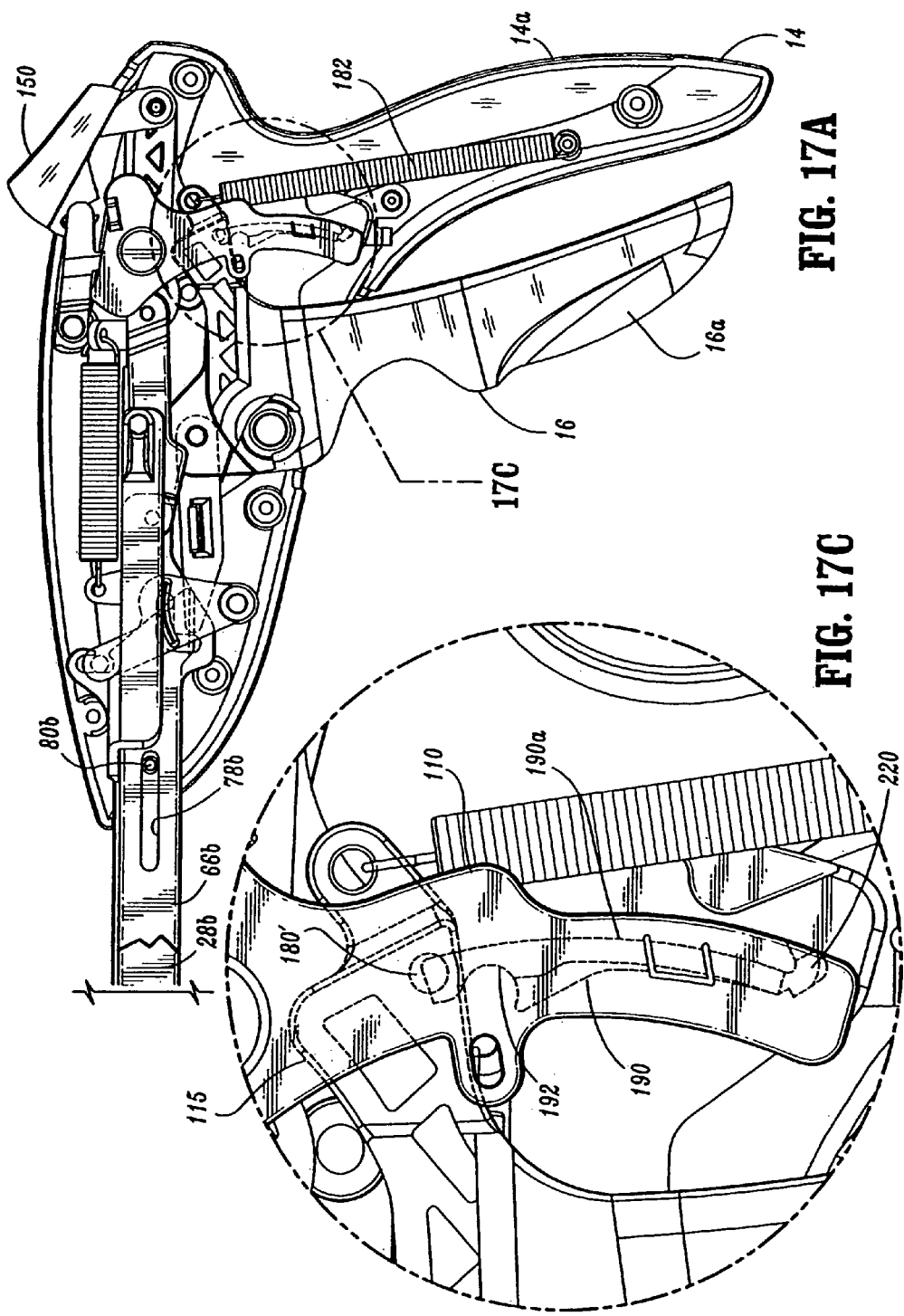
FIG. 17A is a side partial cutaway view of the handle portion of the surgical stapling device shown in FIG. 1 in the approximated position with the left body half-section and frame removed from the handle portion of the device and the trigger in the compressed position.
FIG. 17C is an enlarged view of the indicated area of detail shown in FIG. 17A.

FIGS. 17-17C illustrate the surgical stapling device 10 in the fully approximated position with trigger 16 in the compressed position. As illustrated, extension 115 on trigger 16 has been pivoted to move bi-linkage assembly 111 to the substantially aligned positioned (slightly over-center position) and clamp slide assembly has been fully advanced such that cartridge assembly 20 and anvil assembly 22 are in the approximated position. Once again, note the position of pins 80a and 80b within clamp slide slots 78a and 78b and thrust bar slots 102a and 102b. Because pins 80a and 80b are located at the proximal end of clamp slide slots 78a and 78b, only thrust bar 70 can be advanced further distally. If the alignment pin pusher was manually advanced prior to approximation, disengaging post 94 from C-clip 126, advancement of clamp slides 66a and 66b to the fully advanced position moves post 94 of bell crank 96 back into engagement with C-clip 126. Thus, when clamp slides 66a and 66b are returned to their retracted position, cam slots 140 in clamp slides 66a and 66b pivot bell crank 96 in a direction to move pin pusher 68 to the retracted position.

Referring to FIG. 17B, trigger 16 has been pivoted to remove cam member 180 from cam recess 178 in clamping pawl 108. As bi-linkage assembly 111 moves overcenter to the substantially aligned position, rear link 114 engages abutment member 200 (FIGS. 10-11) formed on clamping pawl 108 and firing pawl 110 to rotate the clamping and firing pawls approximately 10° counter-clockwise. This rotation removes cam surface 176 from the path of cam member 180 during the return of trigger 16 to the non-compressed position.

Referring to FIG. 17C cam member 180' formed opposite to cam member 180 on extension 115 of trigger 16 is now positioned above cam surface 190 of firing pawl 110. As trigger 16 is released by the surgeon and returned to the non-compressed position by spring 182, cam member 180' moves along the backside 190a of cam surface 190. As cam member 180' reaches the bottom edge of backside 190a, cam member 180' moves over a nub 220 formed on firing pawl 110. Movement of cam member 180' over nub 220 provides an audible click and a tactile indication that surgical stapling apparatus 10 is in a fire-ready position.

Figure 18A:
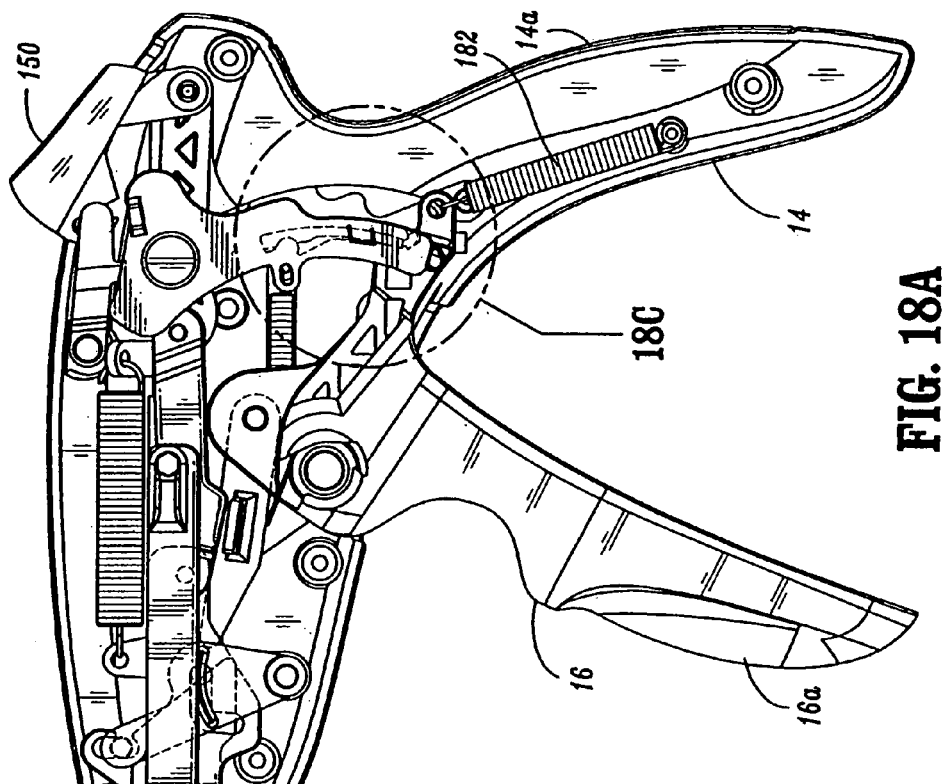
FIG. 18A is a side partial cutaway view of the handle portion of the surgical stapling device shown in FIG. 1 in the fully approximated position with the left body half-section and frame removed from the handle portion of the device and the trigger in a fire-ready position.
Figure 18C:
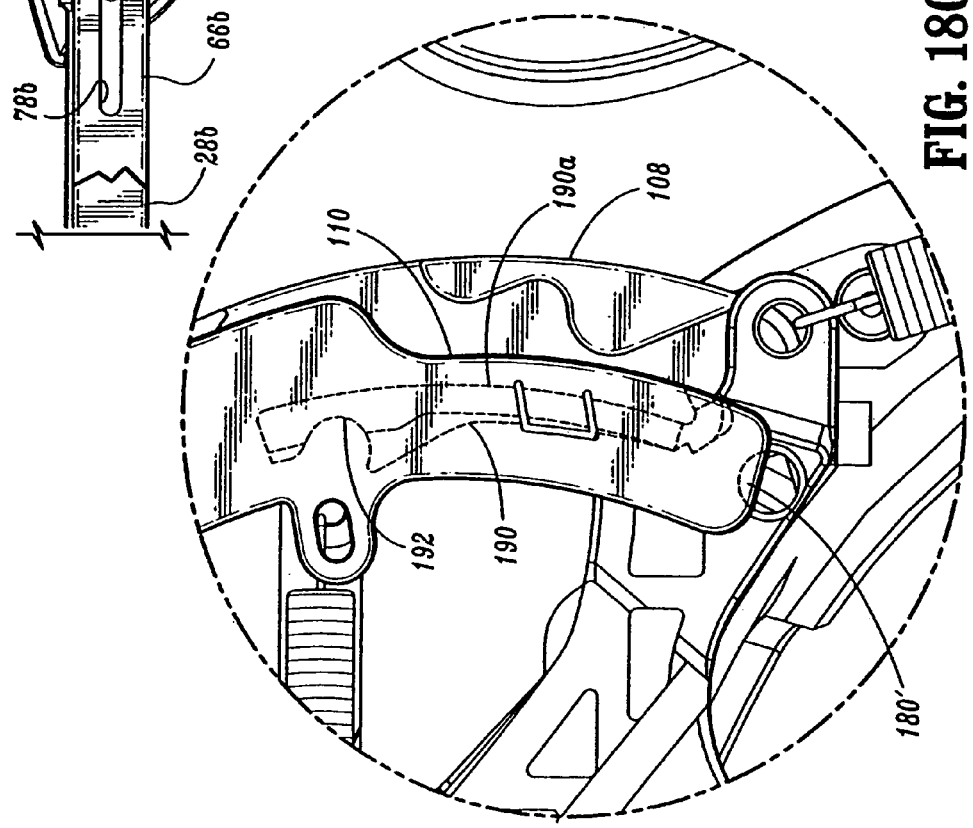
FIG. 18C is an enlarged view of the indicated area of detail shown in FIG. 18A.

FIGS. 18-18C illustrate the surgical stapling device 10 in the fully approximated position with the trigger 16 in the non-compressed position. As illustrated, with thrust bar 70 in an advanced position, notch 104 is now aligned with firing link 106 such that movement of trigger 16 through the firing stroke will effect advancement of thrust bar 70. Referring to FIG. 18C, camming member 180' is now positioned below cam surface 190 of firing pawl 110.

FIGS. 19-19C illustrate surgical stapling instrument 10 after trigger 16 has been moved through the firing stroke. As illustrated, thrust bar 70 has been advanced distally to eject staples from cartridge assembly 20. Note pins 80a and 80b are now positioned adjacent the proximal end of slots 102a and 102b. Referring particularly to FIG. 19C, cam member 180' of extension 115 of trigger 16 has moved up cam surface 190 and is positioned in recess 192. Engagement between cam member 180' and recess 192 prevents spring 182 from returning trigger 16 to the non-compressed position to provide a visual indication to the surgeon that the surgical device has been fired. Movement of cam member 180' into recess 192, also provides an audible indication that firing of the device has occurred.

Figures 20, 20A:
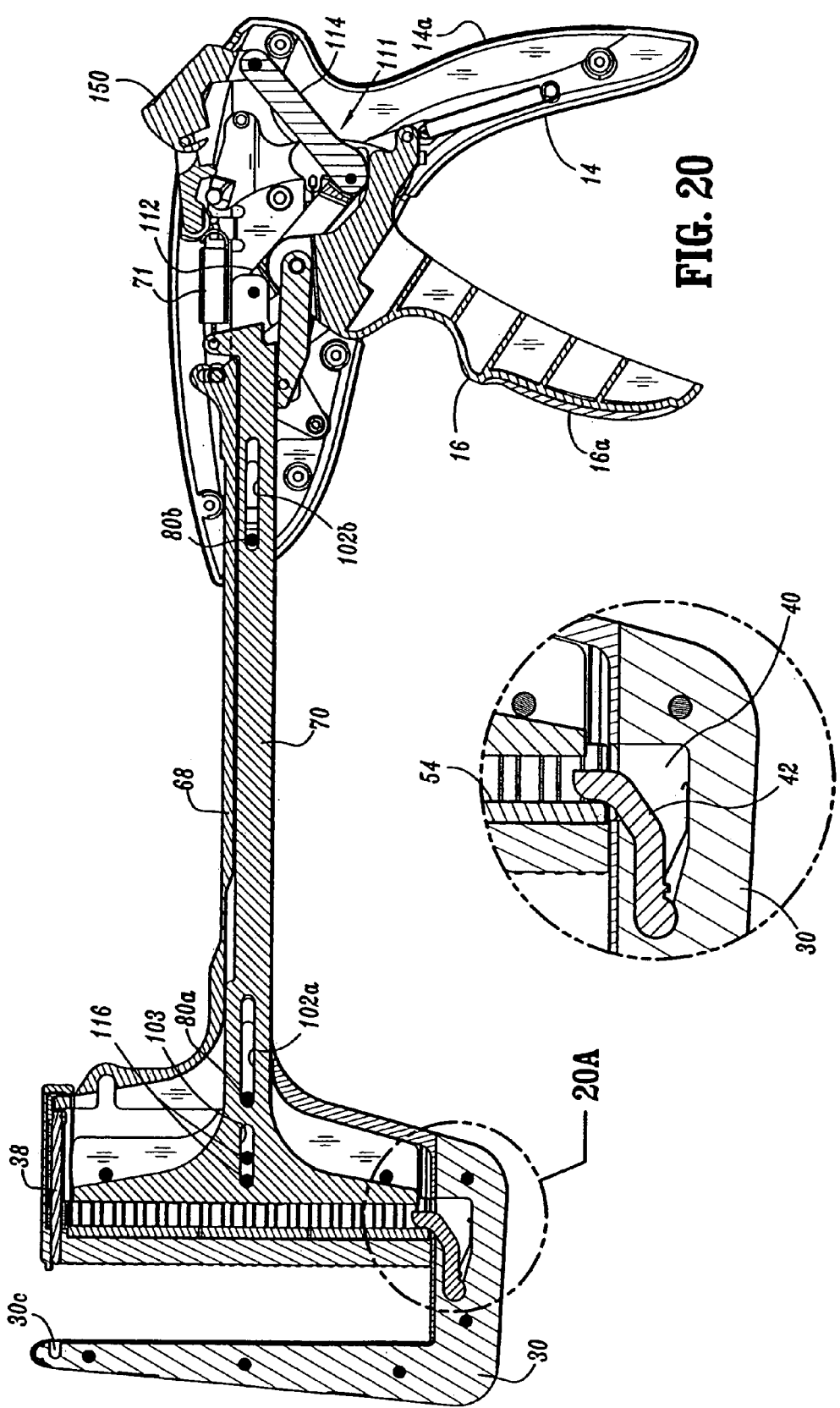
FIG. 20 is a side cross-sectional view of the surgical stapling device shown in FIG. 1 after the staples have been fired from the staple cartridge and the cartridge assembly has been moved to the retracted position.
FIG. 20A is an enlarged view of the indicated area of detail shown in FIG. 20.

FIG. 20 illustrates surgical stapling device 10 after it has been fired and the release mechanism 26 has been depressed to return bi-linkage assembly 111 to the misaligned position. Once bi-linkage assembly 111 is moved back overcenter, spring 71 returns thrust bar 70 and clamp slide members 66a and 66b proximally to return links 112 and 114 to the misaligned position.

As illustrated in FIG. 20A, interlock 42 is normally urged by pusher assembly 54 to a position located within recess 40. After cartridge assembly 20 has been fired, pusher assembly 54 is no longer positioned to bias interlock 42 into recess 40. Until a new cartridge has been inserted into surgical stapling device 10, interlock 42 will extend from recess 40 to prevent thrust bar 70 from being advanced distally.

Figure 22:
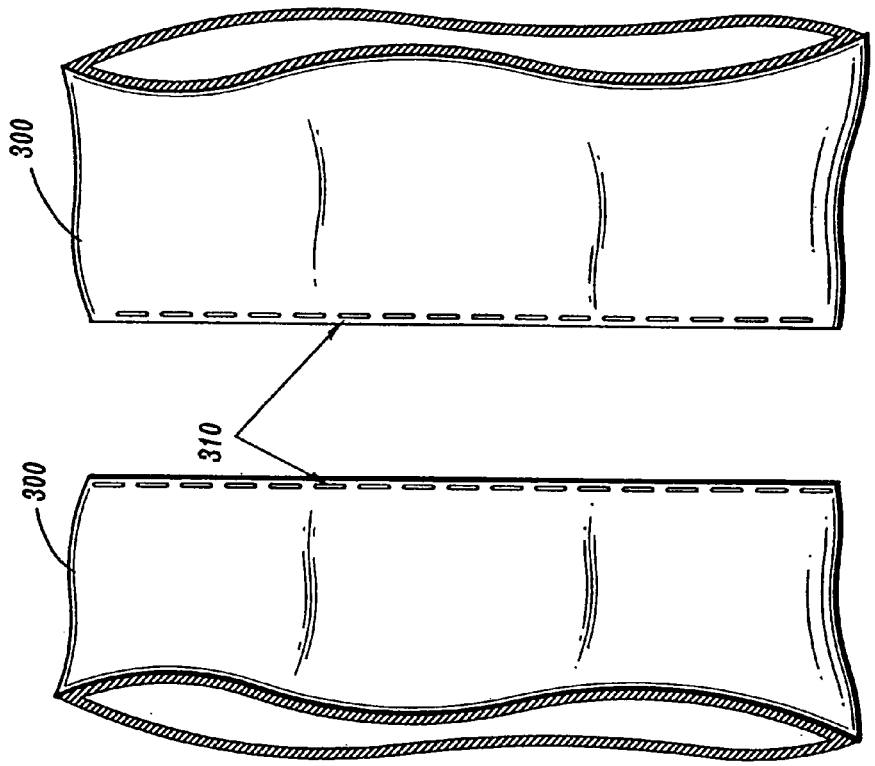
FIG. 22 is a top view of the tissue shown in FIG. 16 illustrating the staple configuration after the tissue has been cut.
Figure 21:
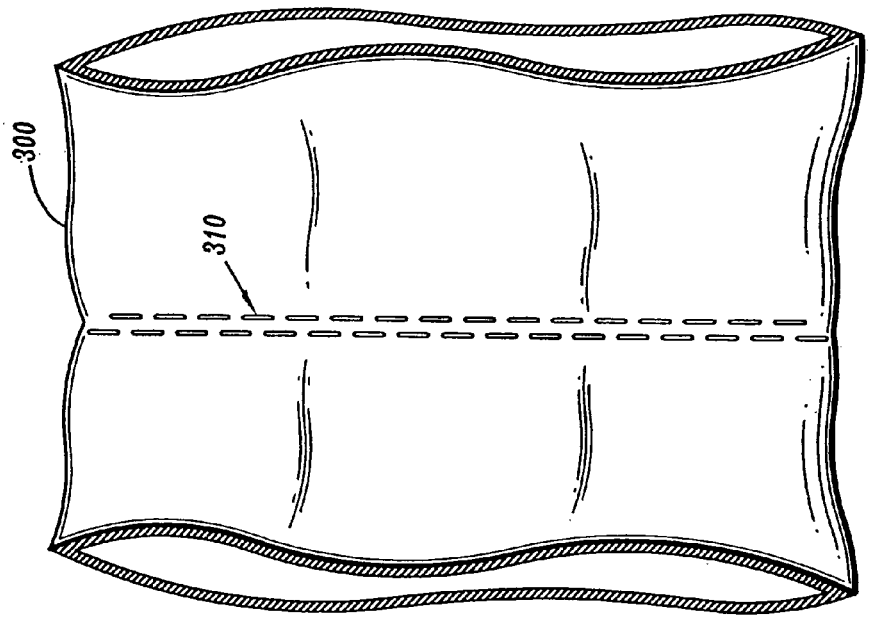
FIG. 21 is a top view of tissue illustrating the staple configuration applied to tissue by the surgical stapling device shown in FIG. 1.

FIG. 21 illustrates tissue 300 having an applied array of staples 310 formed therein. FIG. 22 illustrates tissue 300 after it has been bisected with a scalpel (not shown).

It will be understood that various modifications may be made to the embodiments disclosed herein. For example, the components of the surgical stapling device can be formed of any material suitable for surgical use and having the required strength characteristics. Therefore, the above description should not be construed as limiting, but merely as exemplifications of preferred embodiments. Those skilled in the art will envision other modifications within the scope and spirit of the claims appended hereto.

What is claimed is:

1. A surgical stapling apparatus comprising:
a handle portion;
a body portion extending from the handle portion;
a head portion including an anvil and a cartridge, the cartridge movable in relation to the anvil between an open position and a closed position;
an approximation mechanism operatively connected to the cartridge for moving the cartridge between the open position and the closed position;
an alignment pin assembly including a pusher operatively associated with the approximation mechanism, the pusher being automatically movable in response to actuation of the approximation mechanism between a retracted position and an advanced position; and
a manual engagement member located remotely of the head portion and operatively associated with the alignment pin assembly, the manual engagement member movable for manually advancing the pusher from the retracted position to the advanced position independent of actuation of the approximation mechanism.

2. A surgical stapling device comprising:
a body portion having a longitudinal axis, a proximal portion and a distal portion;
an alignment pin movable between a retracted position and an advanced position;
a cartridge having a plurality of staple pushers to eject staples and an opening to slidably receive the alignment pin;
an anvil assembly having an opening for passage of the alignment pin and having pockets with staple forming surfaces to form staples ejected from the cartridge;
a trigger for approximating the cartridge and anvil assembly; and
a manually actuated member operatively associated with the alignment pin, the manually actuated member advancing the alignment pin from the retracted position to the advanced position independently of the trigger, wherein actuation of the trigger automatically advances the alignment pin from the retracted position to the advanced position when the alignment pin has not previously been advanced by the manually actuated member.

3. The surgical stapling device of claim 2, wherein the cartridge is a removably mounted cartridge and the manually actuated member is spaced proximally from the cartridge.

4. The surgical stapling device of claim 3, wherein the manually actuated member is slidable in a longitudinal direction to advance the alignment pin.

5. The surgical stapling device of claim 3, further comprising a pivotable member pivotable to advance the alignment pin.

6. The surgical stapling device of claim 5, wherein the pivotable member includes a post extending transverse to the longitudinal axis to move the alignment pin distally to the advanced position.

7. The surgical stapling device of claim 5, wherein the pivotable member includes a cam member receivable in a slot of a clamp slide.

8. The surgical stapling device of claim 2, wherein the manually actuated member operatively engages a post extending into a slot extending parallel to the longitudinal axis of the body.

9. The surgical stapling device of claim 2, further comprising a release button.

10. The surgical stapling device of claim 2, further comprising a spring urging the alignment pin to the retracted position.

11. The surgical stapling device of claim 2, further comprising an alignment pin pusher, the alignment pin pusher engaging a proximal end portion of the alignment pin.

12. The surgical stapling device of claim 2, further comprising an elongated member operatively associated with the manually actuated member and the alignment pin.

13. A surgical stapling device comprising:
a body portion;
an anvil located in a distal region of the body portion;
a head portion having a cartridge, the cartridge including an alignment pin movable within the cartridge;
an approximation mechanism, the approximation mechanism operable for repositioning the cartridge from a first position to a second position;
a manual engagement member located proximally of the head portion; and
a pusher movable from a retracted position to an advanced position for moving the alignment pin, the pusher being operably associated with the manual engagement member such that actuation of the manual engagement member results in operation of the pusher independently of the approximation mechanism and automatically actuated in response to the actuation of the approximation mechanism.

14. The surgical stapling device of claim 13, wherein the cartridge is longitudinally spaced from the anvil in the first position and the cartridge is in close cooperative alignment with the anvil in the second position.

15. The surgical stapling device of claim 13, wherein the cartridge includes at least one surgical fastener and is removably mounted to the head portion.

16. The surgical stapling device of claim 13, further including a bell crank operatively connected to the approximation mechanism, the bell crank being positioned to move the pusher.

17. The surgical stapling device of claim 13, wherein the pusher is repositionable in response to actuation of the manual engagement member prior to actuation of the approximation mechanism.

18. The surgical stapling device of claim 13, further comprising a handle portion, the handle portion including a trigger and the approximation mechanism includes at least one clamp slide having a first end configured to support the cartridge and a second end operatively coupled to the trigger such that actuation of the trigger causes movement of the at least one clamp slide to reposition the cartridge from the first position to the second position.

19. The surgical stapling device of claim 18, wherein the manual engagement member is located on the handle portion.

20. The surgical stapling device of claim 13, further including a firing mechanism having a thrust bar with a distal end movable within the cartridge.

21. The surgical stapling device of claim 20, wherein a proximal end of the thrust bar is operatively associated with the handle portion.

22. A surgical stapling device comprising:
a handle portion;
a body portion extending from the handle portion;
a head portion including an anvil and a cartridge, the cartridge being movable from a first position to a second position, wherein the cartridge includes an alignment pin movable within the cartridge;
an approximation mechanism operatively connected to the cartridge, wherein actuation of the approximation mechanism repositions the cartridge from the first position to the second position;
a pusher movable from a retracted position to an advanced position to move the alignment pin; and
a manual engagement member located remotely of the head portion, the manual engagement member operatively associated with the pusher, wherein operation of the manual engagement member repositions the pusher independently of the approximation mechanism, the pusher being repositioned automatically in response to operation of the approximation mechanism.

23. The surgical stapling device of claim 22, further including a bell crank operatively connected to the approximation mechanism, the bell crank being positioned to move the pusher.

24. The surgical stapling device of claim 22, wherein actuation of the manual engagement member manually moves the pusher from the retracted position to the advanced position prior to actuation of the approximation mechanism.

25. The surgical stapling device of claim 22, wherein the handle portion includes a trigger and the approximation mechanism includes at least one clamp slide having a first end configured to support the cartridge and a second end operatively connected to the trigger such that actuation of the trigger causes movement of the at least one clamp slide to reposition the cartridge from the first position to the second position.

26. The surgical stapling device of claim 22, further including a firing mechanism including a thrust bar having a distal end positioned to move within the cartridge.

27. The surgical stapling device of claim 26, wherein a proximal end of the thrust bar is operatively associated with the handle portion.

28. The surgical stapling device of claim 22, wherein the manual engagement member is located on the handle portion.

29. A surgical stapling device comprising:
a handle portion;
a body portion extending from the handle portion;
a head portion including an anvil and a cartridge, the cartridge being movable in relation to the anvil from an open position to a closed position;
an approximation mechanism operatively coupled to the cartridge, wherein actuation of the approximation mechanism repositions the cartridge from the open position to the closed position;
a pusher being movable in response to the approximation mechanism from a retracted position to an advanced position;
means for manually moving the pusher from the retracted position to the advanced position independently of the approximation mechanism, the means located remotely from the head portion; and
activation means for automatically moving the pusher from the retracted position to the advanced position in response to actuation of the approximation mechanism.

30. The surgical stapling device of claim 29, further including a bell crank operatively associated with the pusher, the bell crank being positioned to move the pusher.

31. The surgical stapling device of claim 29, wherein the means for manually moving the pusher includes a manual engagement member.

32. The surgical stapling device of claim 31, wherein the manual engagement member is located on the handle portion.

33. The surgical stapling device of claim 29, wherein the activation means includes a bell crank operatively associated with the approximation mechanism and operatively associated with the pusher.

34. The surgical stapling device of claim 29, wherein the cartridge includes an alignment pin.

35. The surgical stapling device of claim 34, wherein the alignment pin is operatively associated with the pusher.

36. The surgical stapling device of claim 29, wherein the means for manually moving the pusher is located on the handle portion.

37. The surgical stapling device of claim 29, further including a firing mechanism having a thrust bar, the thrust bar having a distal end positioned to move within the cartridge.

38. The surgical stapling device of claim 37, wherein a proximal end of the thrust bar is operatively associated with the handle portion.

39. The surgical stapling device of claim 29, further including at least one post dimensioned to extend through a slot formed in the body portion, the post being slidable within the slot.

40. The surgical stapling device of claim 39, wherein the at least one post is connected to the pusher.

41. The surgical stapling device of claim 40, wherein the at least one post is integrally formed on the pusher.

42. The surgical stapling device of claim 39, wherein the manual engagement member includes a thumb button secured to the at least one post, the thumb button being positioned on the body portion at a location to permit manual advancement of the pusher.

* * * * *